(12) United States Patent
Shen et al.

(10) Patent No.: US 7,258,877 B2
(45) Date of Patent: *Aug. 21, 2007

(54) HERBAL PHARMACEUTICAL COMPOSITION FOR TREATMENT OF CARDIOVASCULAR DISEASE

(75) Inventors: Chung Guang Shen, Foster City, CA (US); Wu-Chang Chuang, Yonghe (TW)

(73) Assignee: SunTen Phytotech Co., Ltd., Taipei (TW)

( * ) Notice: Subject to any disclaimer, the term of this patent is extended or adjusted under 35 U.S.C. 154(b) by 407 days.

This patent is subject to a terminal disclaimer.

(21) Appl. No.: 10/927,196

(22) Filed: Aug. 27, 2004

(65) Prior Publication Data

US 2005/0025843 A1    Feb. 3, 2005

Related U.S. Application Data

(63) Continuation-in-part of application No. 10/164,568, filed on Jun. 10, 2002, now Pat. No. 6,793,944.

(30) Foreign Application Priority Data

Dec. 21, 2001 (TW) .............................. 90131897 A

(51) Int. Cl.
*A61K 36/25* (2006.01)
*A61K 36/708* (2006.01)
*A61K 36/00* (2006.01)
*A61K 36/539* (2006.01)

(52) U.S. Cl. ...................... 424/728; 725/773

(58) Field of Classification Search ................ None
See application file for complete search history.

(56) References Cited

U.S. PATENT DOCUMENTS

| 5,318,798 | A | * | 6/1994 | Uchida et al. ......... 427/213.35 |
| 5,443,839 | A |   | 8/1995 | Meybeck |
| 6,117,838 | A | * | 9/2000 | Przybelski ..................... 514/6 |
| 6,274,177 | B1 |  | 8/2001 | Wu et al. |
| 6,340,480 | B1 |  | 1/2002 | Duckett et al. |
| 2003/0045776 | A1 | * | 3/2003 | Alferness et al. ............. 600/37 |
| 2003/0161842 | A1 | * | 8/2003 | Wang et al. ........... 424/195.15 |

OTHER PUBLICATIONS

Yokozawa et al. Effects on the Proliferation of Smooth Muscle Cells of Oriental Medical Prescription Used for the Treatment of Arteriosclerosis; Natural Medicines 50(1) pp. 9-13, 1996.*

(Continued)

*Primary Examiner*—Patricia Leith
(74) *Attorney, Agent, or Firm*—Occhiuti Rohlicek & Tsao LLP

(57) ABSTRACT

The present invention provides an herbal pharmaceutical composition comprising extracts of the root of scutellaria, the rhizome of coptis, the root and rhizome of rhubarb, and the root of ginseng (or American ginseng). The herbal pharmaceutical composition is effective in treating hypertension or ischemia, protecting vascular endothelia from degeneration, and lowering blood pressure or maintaining stable blood pressure.

11 Claims, 17 Drawing Sheets

OTHER PUBLICATIONS

Simmons, David L. et al., Molecular Cloning of CD31, A Putative Intercellular Adhesion Molecule Closely Related to Carcinoembryonic Antigen; J. Exp. Med., The Rockefeller University Press, vol. 171, Jun. 1990 p. 2147-2152.

Gerlier, D. et al., Use of MTT colorimetric assay to measure cell activation; J Immunol Methods, Nov. 20, 1986;94, (1-2); 57-63 (abstract).

Denizot, F., Rapid colorimetric assay for cell growth and survival. Modifications to the tetrazolium dye procedure giving improved sensitivity and reliability; J Immunol Methods, May 22, 1986;89 (2):271-7 (abstract).

* cited by examiner (A) 
(B)

(C) 
(D)

HERBAL PHARMACEUTICAL COMPOSITION FOR TREATMENT OF CARDIOVASCULAR DISEASE

RELATED APPLICATIONS

The present invention is a Continuation-In-Part (CIP) application of U.S. patent application Ser. No. 10/164,568 filed Jun. 10, 2002 now U.S. Pat. No. 6,793,944, which claims priority of Taiwanese application number 90131897, filed on Dec. 21, 2001. The contents of both applications are herein incorporated by reference.

FIELD OF THE INVENTION

The present invention relates to a pharmaceutical composition which contains extracts from the root of scutellaria (Radix Scutellariae), the rhizome of coptis (Rhizoma Coptidis), the root/rhizome of rhubarb (Radix et Rhizoma Rhei), and the root of ginseng (Radix Ginseng) for improvement of vasodilation and/or maintenance of normal vasodilation; lowering blood pressure and maintenance of stable blood pressure, and protection of endothelial cells in blood vessels from degeneration. The present invention also relates to the methods of preparing and using the herbal pharmaceutical composition.

BACKGROUND OF THE INVENTION

Based on data from the World Health Organization (WHO), cardiovascular diseases contribute to a third of global deaths in 1999 and are estimated to be the leading cause of death in developing countries by 2010. Cardiovascular diseases are the name for a group of disorders in the heart and blood vessels, including, but not limited to, hypertension (high blood pressure), coronary heart disease (heart attack), cerebrovascular disease (stroke), peripheral vascular disease, heart failure, rheumatic heart disease, congenital heart disease, and cardiomyopathies.

Hypertension is by far the most prevalent cardiovascular disease. It is estimated that more than a third of Americans aged 45 or older have high blood pressure and, among them, more than 50% are aged 60 or older. Untreated hypertension can lead to serious and life-threatening complications, e.g., stroke, coronary heart disease, arteriosclerosis, atherosclerosis, heart failure, kidney failure and blindness.

As indicated in the United States Seventh Report of the Joint National Committee (JNC VII) on High Blood Pressure, current treatment for hypertension includes diuretics, α-blockers, β-blockers, calcium channel blockers, ACE inhibitors, and angiotensin antagonists. These agents can be used as monotherapy or in combination. However, most of these agents ameliorate the symptoms but not curing the diseases. These agents are also frequently accompanied with side effects.

One of the major mechanisms for causing human hypertension is the dysfunction of endothelium. Endothelium is the layer of epithelial cells that lines the cavities of the heart and of the blood and lymph vessels. Its main role is to modulate both vascular tone and structure by producing vasodilator and vasoconstrictor mediators.

When activated by specific agonists such as acetylcholine, endothelial cells produce nitric oxide ("NO"), a labile substance derived by L-arginine degradation through the activity of the endothelial NO synthase ("eNOS"). NO is a powerful relaxing agent which also inhibits platelet aggregation and smooth muscle cell proliferation.

Under pathological conditions, such as hypertension or aging, agonist-induced stimulation of endothelium leads to activation of a cyclooxygenase pathway and consequent production of cyclooxygenase-dependent factors, including thromboxane $A_2$ or prostaglandin $H_2$, or free radicals (such as superoxide anions). Dysfunctional endothelium can also cause vascular damage, in particular, atherosclerosis.

There are two isoforms of cyclooxygenase, cyclooxygenase 1 and 2 (COX-1 and COX-2), also referred to as prostaglandin endoperoxide synthase 1 and 2, which are key enzymes in the conversion of arachidonic acid to prostaglandins, thromboxanes and other eicosanoids. It is believed that COX-1 and COX-2 have different physiologic functions due to striking differences in their tissue expression and regulation. COX-1 is a constitutive enzyme that is present at all times in the body and is responsible for the production of cytoprotective prostaglandins important for homeostatic functions, such as maintaining the integrity of the gastric mucosa, mediating normal platelet function, and regulating renal blood flow. In contrast, COX-2 is a rapidly inducible form of cyclooxygenase that leads to the production of proinflammatory prostaglandins. While COX-2 expression is highly restricted under basal conditions, it is dramatically up-regulated during inflammation. The involvement of COX-2 and the elevated production of prostaglandins are associated with a variety of diseases and disorders, such as brain ischemia and cancers, as well as diseases and disorders in which elevated levels of NO is present.

NO modulates the activity of COX-2 and participates in inflammatory and autoimmune-mediated tissue destruction. The effect of NO on COX-2 is dose-dependent. Low levels of NO activate COX-2. In contrast, large amounts of NO produced by inducible nitric oxide synthase ("iNOS") can inhibit the induction of COX-2 and suppress the formation of COX-2 metabolites.

iNOS is expressed in the myocardium after myocardial infarction (MI) and in heart failure. Myocardium is the middle and thickest layer of the heart wall composes of cardiac muscle. Upregulation or overexpression of iNOS is associated with mild inflammatory cell infiltrate, cardiac fibrosis, hypertrophy, and dilatation. Cardiac hypertrophy is a significant risk factor for the development of congestive heart failure (CHF). Overexpression of iNOS results in overproduction of NO, causing myocardial dysfunction and CHF.

CHF is a form of heart disease in which weakened heart function exists with concomitant edema. CHF has many different causes, including narrowing of the arteries supplying blood to the heart muscle (coronary heart disease), prior heart attack (myocardial infarction) resulting in scar tissue large enough or located so to interfere with normal electrocardiac function, high blood pressure, etc. CHF is one of the most serious cardiovascular diseases affecting adults. Over 4 million people have CHF and the incidence is on the rise. The incidence of this disease or condition is increasing with the aging of the population and is currently the most common cause for hospital admission in the elderly. The total U.S. healthcare expenditure on CHF is over five billion dollars per year.

Atrial fibrillation (AF) is atrial arrhythmia characterized by rapid randomized contractions of the atrial myocardium, causing a totally irregular, often rapid ventricular rate. AF may persist due to structural changes in the atria that are promoted by inflammation. C-reactive protein (CRP) is a marker of systemic inflammation which predicts cardiovascular events and stroke, a common sequela of AF. CRP also induces adhesion molecule expression by endothelial cells.

While a panacea has been hunted for in western medicine for years, researchers turn to traditional Chinese herbal medicine for medications of various diseases. Chinese herbal medicine has existed and been use for treating various diseases for thousands of years.

For example, San-Huang-Hsie-Hsin-Tang is an ancient herbal decoction which was first described in Chin-Kuei-Yao-Lueh (translated into English as "the Prescriptions From the Golden Chamber") for "purging fire and clearing the three torsos" and wherefore it is indicated for insufficient cardiac "Chi," hematemesis, and epistaxis. The decoction is made of equal amounts of the root of scutellaria (Radix Scutellariae), the rhizome of coptis (Rhizoma Coptidis), and the root and rhizome of rhubarb (Radix et Rhizoma Rhei). The decoction has a bitter taste and with a cold nature. The decoction is intended for patients with congestion, flush up, fidgets, shoulder stiffness, gastric obstructive depression, constipation, and forceful pulse. However, the decoction is contraindicated or not suitable for patients with symptoms of prolonged bleeding, marked anemia, and minute-weak pulses.

U.S. Pat. No. 5,443,839 discloses a composition having anti-inflammatory, anti-allergic or anti-aging activity comprising, inter alia, an extract of Scutellaria. There is no indication that the composition is effective in treating cardiovascular disease and hypertension.

U.S. Pat. No. 6,274,177 discloses a method of preparing an extract from Zingiber officinale, which is potent in anti-inflammation and anti-platelet aggregation. There is no indication that the herbal composition is effective in treating cardiovascular disease and hypertension.

U.S. Pat. No. 6,340,480 discloses a composition and method for treating circulatory conditions including hypertension by promoting systemic vascular relaxation and dilation. The composition is a natural combination of L-arginine, ginseng, and Zizyphi fructus in an orally or topically administered form. The combination works synergistically to synthesize NO and thereby promote systemic vascular relaxation and dilation. The combined constituents may work to maintain a critical threshold level of NO in areas that cannot themselves produce it, thereby promoting systemic vascular relaxation and dilation in order to reduce hypertension. However, it is not clear whether the herbal composition is effective in treating cardiovascular disease.

In the parent application, U.S. patent application Ser. No.10/164,568, an herbal pharmaceutical composition is described, which contains an extract of the root of scutellaria (Radix Scutellariae), an extract of the rhizome of coptis (Rhizoma Coptidis), an extract of the root/rhizome of rhubarb (Radix et Rhizoma Rhei), and the powder of the root of ginseng (Radix Ginseng) or American ginseng (Radix Panacis Quinquefolii). This herbal pharmaceutical composition is effective in both prophylaxis and treatment of cardiovascular diseases. The composition is also non-toxic and thus can be used by patients in all ages and physical conditions, including the week, the early and the debilitated.

In this CIP application, a slightly different herbal pharmaceutical composition is described, wherein the powder of the root of ginseng (Radix Ginseng) is replaced with an extract from the root of ginseng. The herbal pharmaceutical composition of the present invention not only demonstrates similar effects in both prophylaxis and treatment of cardiovascular diseases, but also exhibits superior function on improving vasodilation and/or maintaining normal vasodilation; and protective function on endothelial cells in the blood vessels, particularly by preventing degeneration of endothelial cells.

SUMMARY OF THE INVENTION

The present invention provides an herbal pharmaceutical composition which comprises extracts of Radix Scutellariae (root of scutellaria), Rhizoma Coptidis (rhizome of coptis), Radix et Rhizoma Rhei (root/rhizome of rhubarb), and Radix Ginseng (root of ginseng), wherein the extracts are produced by individually extracting the root of scutellaria, the rhizoma of coptis, the root/rhizome of rhubarb, and the root of ginseng by a solvent which is at least one selected from the group consisting of water and alcohol.

The root of scutellaria, the rhizome of coptis, the root and rhizome of rhubarb, and the root of ginseng of the pharmaceutical composition of the present invention are at a weight ratio of about 1-2:1-2:1-2:1-2, preferably at about 1:1:2:1. Preferably, the root of scutellaria and the rhizome of coptis are extracted by water at about 98±5° C.; the root/rhizome of rhubarb is extracted by about 95% ethyl alcohol at about 70±5° C.; and the root of ginseng are extracted by about 50% ethyl alcohol at about 70±5° C.

The extracts of the pharmaceutical composition of the present invention are individually processed by extraction, filtration and condensation. This allows each extract of the individual herb to be turned into a condensed paste. Each of the condensed paste then is further dried into individual condensed powders. Optionally, a pharmaceutically acceptable carrier can be added before the condensation step to facilitate the drying of the condensed paste. The condensed powders of each individual herbs are further mixed, combined and granulated to form granules, which can be capsulated.

The pharmaceutical composition of the present invention has the effects of improving vasodilation and/or maintain normal vasodilation in a mammal; lowering and/or maintaining stable blood pressure, and protecting the endothelial cells in blood vessels from degeneration. Vasodilation refers to dilation of a vessel, especially dilation of arterioles leading to increased blood flow to a part of the vessel.

The present invention further provides a method for preparing the herbal pharmaceutical composition of the present invention, which includes the following steps: (1) individually extracting the root of scutellaria, the rhizome of coptis, the root/rhizome of rhubarb, and the root of ginseng with the solvent (which consists of water or ethyl alcohol, or a mixture thereof) to separately form an extract of root of scutellaria, an extract of rhizome of coptis, an extract of root/rhizome of rhubarb, and an extract of root of ginseng; (2) separately filtering and condensing each of the individual extract from the root of scutellaria, the rhizome of coptis, the root/rhizome of rhubarb, and the root of ginseng to form separate herbal paste for the root of scutellaria, the rhizome of coptis, the root/rhizome of rhubarb, and the root of ginseng; (3) separately drying each of the separate herbal paste for the root of scutellaria, the rhizome of coptis, the root/rhizome of rhubarb, and the root of ginseng to form concentrated powders of each of the root of scutellaria, the rhizome of coptis, the root/rhizome of rhubarb, and the root of ginseng; (4) mixing each of the concentrated powders for the root of scutellaria, the rhizome of coptis, and the root/rhizome of rhubarb, and said concentrated powders of ginseng to form an herbal powder mixture; and (5) granulating said herbal powder mixture to form granules of said herbal pharmaceutical composition. Optionally, a pharmaceutically acceptable excipient or carrier can be added to each of the individual herbal paste before the drying process. The granules of the pharmaceutical composition can be encapsulated.

Finally, the present invention provides methods for improving vasodilation and/or maintaining normal vasodilation in a mammal, such as a human; for lowering and/or maintaining stable blood pressure in a mammal, such as a human; and for protecting the endothelial cells in blood vessels from degeneration, in a mammal, such as a human, by administering to the mammal an effective amount of the herbal pharmaceutical composition of the present invention. The herbal pharmaceutical composition is preferably administered to the mammal orally.

DETAILED DESCRIPTION OF THE INVENTION

Figure 1:
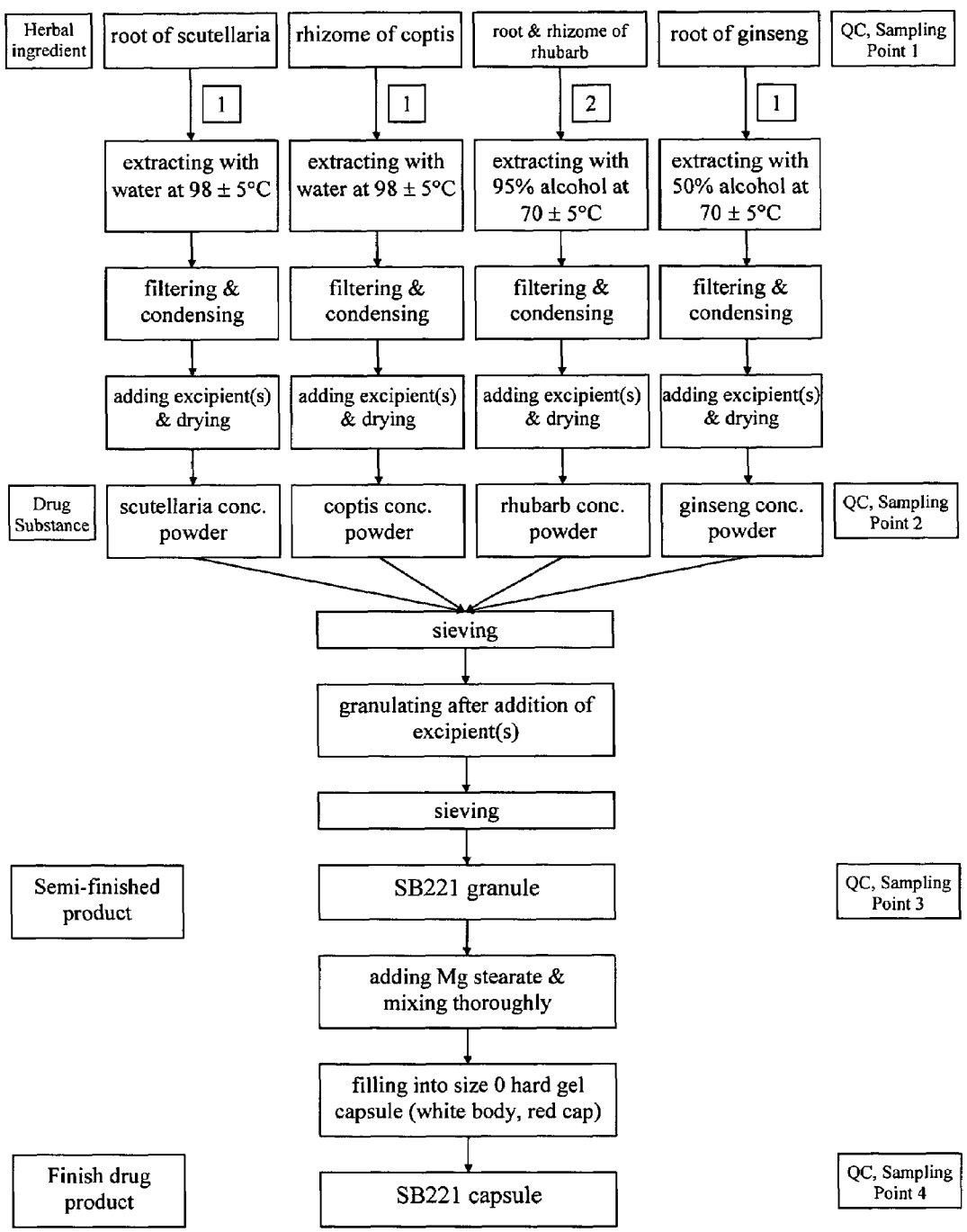
FIG. 1 shows a flow chart of the manufacturing process for producing the pharmaceutical composition of the present invention. QC: Quality control. There were four sample collection points in the QC process, which were (a) the herbal ingredient stage (which contained raw materials); (b) the drug substance stage (which contained concentrated powder of each herb); (c) the semi-finished product stage (which contained mixed granules); and (d) the finished drug product stage (which contained capsule).

The present invention provides a novel herbal pharmaceutical composition for preventing and treating cardiovascular diseases, which are suitable for patients of all ages and various physical conditions, including elderly and debilitated.

Recent progress in the scientific and medical understanding of the cardiovascular diseases provide more knowledge on the involvement of endothelial damages, nitric oxide (NO), inflammation reactions and C-reactive protein (CRP) in these diseases. NO produced in the endothelium by the endothelial nitric oxide synthase (eNOS) is not only a potent vasodilator but also inhibits platelet aggregation, smooth muscle cell proliferation, monocyte adhesion and adhesion molecule expression, thus, maintain the integrity of the endothelial tissues. Production of cyclooxygenase (COX)-dependent factors, including prostanoids and oxygen free radicals, may be the main cause for endothelial dysfunction. Dysfunctional endothelium can then be one of the main mechanisms causing vascular damage which can further lead to more severe cardiovascular diseases. As inhibition of cyclooxygenase may restore NO-mediated vasodilation in essential hypertension, anti-inflammatory interventions may have therapeutic utility.

During diseased states, e.g., cardiac hypertrophy, myocardial infarction (MI), ischemia, myocarditis and septic shock, overexpression of the inducible nitric oxide synthase (iNOS) leads to increased production of NO. The elevated NO levels can result in more severe complications, e.g., myocardial dysfunction, congestive heart failure and sudden cardiac death.

During the inflammation process, an acute-phase reactant, C-reactive protein (CRP), is formed. CRP, frequently used as a systemic inflammation marker, promotes the expression of the adhesion molecules and may plays a direct role in the pathogenesis of vascular inflammation, particularly atherosclerosis. CRP has been associated with vascular risk factors and with prevalent and incident atherothrombotic cardiovascular diseases, i.e., coronary heart disease, stroke, and peripheral arterial disease.

A new approach for treatment of cardiovascular diseases should consider all aspects of the diseases. For example, in addition to the anti-hypertensive activity, the new medicine should not only be able to protect healthy endothelium but also improve the functions of dysfunctional endothelium.

The present invention provides an herbal pharmaceutical composition that has the functions of reducing high blood pressure, maintaining normal blood pressure; improving vasodilation and/or maintaining normal vasodilation; and protecting vascular endothelial cell from degeneration, so as to treat and prevent cardiovascular diseases.

The herbal pharmaceutical composition of the present invention contains four herbs, which are the root of scutellaria, the rhizome of coptis, the root and rhizome of rhubarb, and the root of ginseng. The herbs used in the compositions can be any variants of the herbs mentioned above. For example, the root of scutellaria has three closely related variants, which are, Scutellaria baicalensis Georgi, Scutellaria viscidula Bge., and Scutellaria amoena C. H. Wright. The rhizome of coptis has four closely related variants, which are, Coptis chinensis Franch., Coptis deltoidea C. Y. Cheng et Hsiao, Coptis teetoides C. Y. Cheng, and Coptis omeiensis (Chen) C. Y. Cheng. The root and rhizome of rhubarb has three closely related variants, which are Rheum palmatum L., Rheum tanguticum Maxim., and Rheum officinale Baill.

The pharmaceutical effect of scutellaria is in the dried root, which has the pharmaceutical name of Radix Scutellariae. Scutellaria belongs to the family of Labiatae. The herb is mainly produced in the provinces of Hebei, Shanxi, and inner Mongolia of China. The best harvest seasons for the herb are in spring or autumn. The root of scutellaria is dried under the sunlight, sliced, and used unprepared or stir-baked with wine or stir-baked to charcoal. The herb is bitter in flavor and cold in property. According to traditional Chinese medicine, the herb can be used to cure diseases in lung, gallbladder, stomach, and large intestine channels. Specifically, the herb can be used to remove damp-heat, counteract toxicity, arrest bleeding, and prevent abortion in patients.

The root of scutellaria contains active ingredients which include, but are not limited to, baicalin, oroxylin A-glucuronide, wogonin-7-O-glucuronide, baicalein, wogonin, and oroxylin A. Baicalin can be used as a denominator for qualitative or quantitative control of the herb.

The pharmaceutical effect of coptis is in the dried rhizome of coptis, which has the pharmaceutical name of Rhizoma Coptidis. Coptis belongs to the family of Ranunculaceae. It is mainly produced in the provinces of Sichuan, Hubei, and Yunnan of China. The preferred harvest season is in autumn. The rhizome of coptis is dried under the sunlight after the rootlets and earth have been removed and used unprepared or stir-baked with ginger juice. The herb is bitter in flavor and cold in property. According to traditional Chinese medicine, the herb can be used to cure diseases in the heart, stomach, liver, and large intestine channels.

The rhizome of coptis contains active ingredients, which include, but are not limited to, berberastine, columbamine, jatrorrhizine, epiberberine, coptisine, palmatine, and berberine. Berberine can be used as a denominator for the qualitative or quantitative control of the herb.

The pharmaceutical effect of rhubarb, is in the dried root and rhizome of rhubarb, which has the pharmaceutical name of Radix et Rhizoma Rhei. Rhubarb belongs to the family of Polygonaceae. It is mainly produced in the provinces of Qinghai and Sichuan of China. The root and rhizome of rhubarb is dug in the late autumn when its stem and leaves begin to wither, or in the early spring before the plant begins to sprout. The harvested herb is dried and sliced. The root and rhizome of rhubarb can be used unprepared, stir-baked with wine, or carbonized. It is bitter in flavor and cold in property. According to traditional Chinese medicine, the root and rhizome of rhubarb can cure diseases in spleen, large intestine, liver, and heart channels.

The root and rhizome of rhubarb contains active ingredients, which include, but are not limited to, sennoside B, sennoside A, aloe-emodin, rhein, emodin, and chrysophanol. Sennoside A and/or emodin can be used as denominators for qualitative or quantitative control of the herb.

There are two kinds of ginseng, Radix Ginseng (root of ginseng) and Radix Panacis Quinquefolii of American ginseng, Panax quinquefollum L). Radix Ginseng (root of ginseng) is used in the herbal pharmaceutical composition of the present invention. Radix Ginseng is Panax ginseng C. A. Mey, belonging to the family of Araliaceae. Ginseng (Radix Ginseng) is mainly produced in the provinces of Jilin, Liaoning, and Heilongjiang of China. Ginseng produced in Fusong of Jilin is particularly of good quality. The herb can also be cultivated, which is called "garden ginseng," as opposed to "mountain ginseng" which refers to the ginseng found in the wild. Cultivated ginseng is harvested in autumn. The harvested ginseng is dried in the sun or roasted, which is called "sun-dried ginseng," or dried after being steamed, which is called "red ginseng," or soaked in syrup, which is known as "sugar-processed ginseng." The fibrous rootlets are known as ginseng rootlets. Wild ginseng dried in the sun is known as sun-cured wild ginseng. The herb is sliced for use. The herb has a sweet and slightly bitter flavor and is neutral in property. According to traditional Chinese medicine, ginseng is particularly good for curing diseases in spleen, lung, and heart channels.

The pharmaceutical effects of ginseng are in its dried root. Ginseng also has effects on central nervous system. It enhances both stimulatory and inhibitory processes in the central nervous system, thereby improving the adaptability of nervous responses. Ginseng can also lower serun glucose and cholesterol. It also shows therapeutic and preventive effect on peptic ulcer.

The active ingredients in the root of ginseng include, but are not limited to, ginsenoside Rg1, ginsenoside Re, and ginsenoside Rb1, among which ginsenoside Rb1 can be used as a denominator for qualitative or quantitative control of the herb.

The pharmaceutical names, botanical names, family names, common descriptions, and major ingredients of the herbs used in the present invention are shown in Table 1.

TABLE 1

Herbs of the Present Pharmaceutical Composition

| Pharmaceutical Name | Botanical Name | Family | Common Description | Major Ingredients |
|---|---|---|---|---|
| Radix Scutellariae | Scutellaria baicalensis Georgi | Labiatae | scutellaria or scute | baicalein, baicalin, wogonin, wogonin-7-0-glucuronide, neobaicalein, oroxylin A glucuronide, camphesterol, β-sitosterol, benzoic acid |
| Rhizoma Coptidis | Coptis chinensis Franch., C. deltoidea C. Y. Cheng, C. omeiensis (Chen) C. Y. Cheng, or C. teetoides C. Y. Cheng | Ranunculaceae | coptis rhizome | berberine, coptisine, worenine, palmatine, columbamine, obacunone, obaculactone, palmatine, jatrorrhizine, magnoflorine, ferulic acid |
| Radix et Rhizoma Rhei | Rheum palmatum L. or R. tanguticum Maxim. et Reg. (used in north China) or R. officinale Baill. (used in south China) | polygonaceae | rhubarb root and rhizome | derivatives of anthraquinone glycosides including chrysophanol, emodin, aloe-emodin, rhein, and physcion, rheum tannic acids, gallic acid, catechin, tetrarin, glucogallin, cinnamic acid, rheosmin, fatty acids, calcium oxalate, glucose, fructose, sennoside A, B, and C |
| Radix Ginseng | Panax ginseng C. A. Mey | Araliaceae | ginseng, red ginseng | panaxatriol, panaxadiol, other panoxisides, panoquilon, panaxin, ginsenin, α-panaxin, protopanaxadiol, protopanaxtriol, panacene, panaxynol, panaenic acid, panose, dammarane, glucose, fructose, maltose, sucrose, nicrotinic acid, riboflavin, thiamine |

Traditionally, Chinese herbal medications which can include ingredients of botanical, animal or mineral sources can be categorized into the following dosage forms based on the methods of preparation: wán (pills), sǎn (powders), gāo (syrups, soft extracts or plasters), dān (special pills or vermilion pills) and tāng (decoctions). Among them, decoctions and powders are the most common dosage forms. Traditionally, the decoctions are prepared by mixing the herbal ingredients of the herbal formula and then boiling the mixture in water or other media. The powder dosage forms are prepared by mixing the herbal ingredients in the herbal formula and directly grinding the mixture into powders. Conventional condensed Chinese medicines are prepared by gathering the herbal ingredients according to the herbal formula, combining and mixing the ingredients, boiling the mixture, filtering, condensing, adding suitable amounts of excipients, granulating, and finally preparing into pills, powders, capsules, and tablets.

Many factors affect the quality of herbal preparations, including, but not limited to, the location and condition of cultivation, timing and method of harvesting, selection, storage, method of preparation. Current practice of manufacturing Chinese herbal medicines generally collects samples of raw herbs, semi-finished product and finished product for the quality control purpose. As illustrated in FIG. 1, in order to provide a better quality control, the present invention utilizes 4-point sampling at the herbal ingredients stage (QC, Sampling Point 1, FIG. 1); the drug substance stage (QC, Sampling Point 2); the semi-finished product stage (QC, Sampling Point 3); and the final finished product stage (QC, Sampling Point 4), to ensure that the quality of the pharmaceutical composition is consistent and well-controlled.

The samples taken from each point of the manufacturing process were subject to High Performance Liquid Chromatography (HPLC) to determine the content of each herb for the purpose of ensuring quality of individual herbal ingredients. The HPLC method and the test results of the herbal components of the present invention are described as follows:

A. Preparation of Herbal Extracts for HPLC 1. 0.5 gram of the samples of the herbal component was precisely weighed and placed in a 50-mL sample bottle.

2. 20 mL of 70% methanol was added to the sample bottle of (1).

3. The mixture of (2) was sonicated at room temperature for 15 minutes and further shaked in a 40° C. water bath at 160 rpm for 20 minutes; the sample was then sat for 30 minutes or more until two layers of the solution was formed.

4. The clear, upper layer of the solution was taken out and passed through a 0.45 μm PVDF filter made by Whatman, England.

5. About 20 μL of the filtered solution was injected into the HPLC for quantitative analysis.

B. Instruments for HPLC Analyses

The instruments used include Waters 600E Pump, Waters 717Plus Autosampler, and Waters 996 Photodiode Array Detector.

C. HPLC Conditions and Results of Individual Herbs

1. Rhubarb (a) HPLC conditions:

Guard column: Lichrospher RP-18 endcapped (5 μm, 4.0 ID×10 mm, Merck, German)

Column: Symmetry Shield RP 18 (5 μm, 4.6 ID×250 mm, Waters, USA)

Column Termperature: 40° C.

Mobile Phase: A: 0.5% acetic acid ($CH_3COOH$) in water B: acetonitrile ($CH_3CN$)

Elution Gradients:

| Time (minutes) | A (%) | B (%) | Linearity |
|---|---|---|---|
| 0 | 86 | 14 | * |
| 40 | 75 | 25 | linear |
| 60 | 55 | 45 | linear |
| 70 | 55 | 45 | linear |
| 90 | 0 | 100 | linear |
| 100 | 86 | 14 | linear |

Flow rate: 0.85 mL/min

Detection wavelength: 270 nm (b) Results:

The HPLC chromatogram of the root/rhizome of rhubarb contains the indicative ingredients of sennoside B, sennoside A, aloe-emodin, rhein, emodin, and chrysophanol. The retention times and maximum absorption wavelengths of these ingredients are shown Table 2.

TABLE 2

Retention Times and Wavelengths of the Ingredients in Rhubarb

| Compound | Retention Time (minutes) | Maximum absorption wavelength (λmax) |
|---|---|---|
| Sennoside B (SB) | ~38 | 268 nm |
| Sennoside A (SA) | ~46 | 269 nm |
| Aloe-emodin (AL) | ~72 | 277 nm |
| Rhein (RH) | ~87 | 257 nm |
| Emodin (EM) | ~92.5 | 287 nm |
| Chrysophenol (CH) | ~94 | 256 nm |

2. Scutellaria (a) HPLC Conditions:

Guard column: Lichrospher RP-18 endcapped (5 μm, 4.0 ID×10 mm, Merck, German)

Column: Cosmosil 5C18-MS (5 μm, 4.6 ID×250 mm, Nacalai tesque, Japan)

Column temperature: 35° C.

Mobile phase: A: 20 mM $KH_2PO_4$ and 0.01% $H_3PO_4$ in water B: acetonitrile ($CH_3CN$) C: water ($H_2O$)

Elution Gradients:

| Time (minutes) | A (%) | B (%) | C (%) | Linearity |
|---|---|---|---|---|
| 0 | 87 | 13 | 0 | * |
| 25 | 75 | 25 | 0 | Linear |
| 40 | 65 | 35 | 0 | Linear |
| 55 | 0 | 75 | 25 | Linear |
| 60 | 87 | 13 | 0 | Linear |

Flow rate: 1.0 mL/min

Detection wavelength: 280 nm (b) Results:

The HPLC chromatogram of the root of scutellaria contains the indicative ingredients of baicalin, oroxylin A-glucuronide, wogonin-7-O-glucuronide, baicalein, wogonin, and oroxylin A. The retention times and maximum absorption wavelengths of these ingredients are shown in Table 3.

TABLE 3

Retention Times and Wavelengths of the Ingredients in Scutellaria

| Compound | Retention Time (minutes) | Maximum absorption wavelength ($\lambda_{max}$) |
|---|---|---|
| Baicalin (BG) | ~30 | 276 nm |
| Oroxylin A - glucuronide (OG) | ~36 | 269 nm |
| Wogonin-7-O-glucuronide (WG) | ~39 | 272 nm |
| Baicalein (B) | ~51 | 275 nm |
| Wogonin (W) | ~56 | 274 nm |
| Oroxylin A (O) | ~57 | 269 nm |

3. Coptis (a) HPLC Conditions

Guard column: Lichrospher RP-18 endcapped (5 μm, 4.0 ID×10 mm, Merck, German)

Column: Cosmosil 5C18-MS (5 μm, 4.6 ID×250 mm, Nacalai tesque, Japan)

Column temperature: 35° C.

Mobile phase: A: buffered acetonitrile (The buffer contains 50 mM of $CH_3COONa$, 2% $CH_3COOH$, and 5 mM $C_{12}H_{25}OSO_3Na$) B: $H_2O:CH_3CN:CH_3OH=10:45:45$ (v/v)

Elution Gradients:

| Time (minutes) | A (%) | B (%) | Linearity |
|---|---|---|---|
| 0 | 100 | 0 | * |
| 15 | 65 | 35 | linear |
| 30 | 65 | 35 | linear |
| 40 | 100 | 0 | linear |

Flow rate: 0.85 mL/min

Detection wavelength: 270 nm (b) Results:

The HPLC chromatogram of the rhizome of coptis contains the indicative ingredients of berberastine, columbamine, jatrorrhizine, epiberberine, coptisine, palmatine, and berberine. The retention times and maximum absorption wavelengths of these ingredients are shown in Table 4.

TABLE 4

Retention Times and Wavelengths of the Ingredients in Coptis

| Compound | Retention Time (minutes) | Maximum absorption wavelength ($\lambda$max) |
|---|---|---|
| Berberastine (Berber) | ~17 | 264 nm; 357 nm |
| Columnbamine (Col) | ~21 | 264 nm; 345 nm |
| Jatrorrhizine (Jat) | ~21.5 | 264 nm; 345 nm |
| Epiberberine (Epi) | ~22.5 | 267 nm; 357 nm |
| Coptisine (Cop) | ~23.5 | 264 nm; 358 nm |
| Palmatine (Pal) | ~26 | 272 nm; 345 nm |
| Berberine (Ber) | ~27 | 263 nm; 347 nm |

4. Ginseng (a) HPLC conditions

Guard column: Lichrospher RP-18 endcapped (5 μm, 4.0 ID×10 mm, Merck, German)

Column: Cosmosil 5C18-MS (5 μm, 4.6 ID×250 mm, Nacalai tesque, Japan)

Column temperature: 35° C.

Mobile phase: A: 20 mM $KH_2PO_4$ B: $CH_3CN$ C: $H_2O$

Elution Gradients:

| Time (minutes) | A (%) | B (%) | C (%) | Linearity |
|---|---|---|---|---|
| 0 | 80 | 20 | 0 | * |
| 20 | 75 | 25 | 0 | Linear |
| 40 | 65 | 35 | 0 | Linear |
| 55 | 0 | 80 | 20 | Linear |
| 60 | 0 | 20 | 80 | Linear |
| 65 | 80 | 20 | 0 | Linear |

Flow Rate: 1.0 mL/min

Detection Wavelength: 203 nm (b) Results:

The HPLC chromatogram of the root of ginseng contains the indicative ingredients of ginsenoside Rg1, ginsenoside Re, and ginsenoside Rb1. The retention sorption wavelengths of these ingredients are shown in Table 5.

TABLE 5

Retention Times and Wavelengths of the Ingredients in Ginseng

| Compound | Retention Time (minutes) | Maximum absorption wavelength ($\lambda$max) |
|---|---|---|
| Ginsenoside Rg1 (Rg1) | ~23.5 | 204 nm |
| Ginsenoside Re (Re) | ~23.8 | 203 nm |
| Ginsenoside Rb1 (Rb1) | ~38.5 | 203 nm |

Pharmaceutical Compositions

In the pharmaceutical composition of the present invention, the root of scutellaria, the rhizome of coptis, the root and rhizome of rhubarb and ginseng are best prepared by solvent extraction followed by condensing and drying into extracts. Optionally, pharmaceutical excipient(s) can be added to the condensate before drying. Examples include, but are not limited to, corn starch.

In the pharmaceutical composition of the present invention, the weight ratio of the root of scutellaria, the rhizome of coptis, the root and rhizome of rhubarb, and the root of ginseng is about 1-2:1-2:1-2:1-2, most favorably 1:1:2:1.

The pharmaceutical composition of the present invention was prepared by the following procedures (FIG. 1):

(1) Preparation of Herbal Extracts

The herbs are preferred to be individually extracted by a solvent. The solvent can be water or organic solvent that is pharmaceutically acceptable for extraction purpose, or a mixture of water and the organic solvent. The preferred organic solvent is ethyl alcohol. It is preferred that the root of scutellaria and the rhizome of coptis are extracted by water at 98±5° C.; the root and rhizome of rhubarb is by alcohol, especially 95% of alcohol in water (v/v), at 70±5° C.; and the root of ginseng is by alcohol, especially 50% in water (v/v), at 70±5° C. The extracts are further filtered individually.

(2) Preparation of Herbal Pastes

For the herbs that have been prepared by extraction, the individual herbal extracts, are individually filtered. After filtration, the individual herbal extracts are separately condensed under reduced pressure in a water bath (maintained at 50° C.) until an individual herbal paste is formed.

(3) Preparation of Concentrated Powders

The condensates are preferably individually dried to produce the concentrated powders. Optionally, pharmaceutically suitable excipient(s) can be added to the condensate and the resultant mixture is dried to produce the extract (drug substance). The excipients are preferably polysaccharide products, which include, but are not limited to, starch, amylose, amylopectin, gelatin, starch 1500, sodium starch glycolate, cellulose, microcrystalline cellulose, hydroxypropylcellulose (HPC), carboxymethyl-cellulose (CMC), croscarmellose, hydroxypropylmethylcellulose (HPMC), and chitosan. The most favorable excipient is corn starch.

(4) Preparation of Granules

The concentrated powders of each the herbs are mixed and passed through a sieve to ensure that the sizes of the powder mixture are within certain ranges. Additionally, pharmaceutically suitable excipient(s), such as magnesium stearate, are added to the powder mixture and the mixture are thoroughly mixed and granulated. The granulation is proceeded with a heat-dry step using a Flow bed. The resultant granules are passed through a sieve to ensure the sizes of the granules are within certain ranges to form the semi-finished product. Furthermore, the semi-finished granule product can be mixed thoroughly with pharmaceutically suitable excipient(s), e.g., magnesium stearate, and processed into tablet, bolus, powder, capsule, and granule by means of formulation which is well-known to those ordinary skill in the art, particularly in the pharmaceutical industry.

The following examples are for illustrative purpose and are not intended to limit the scope of the invention. Reasonable variations, such as those understood by reasonable artisans, can be made herein without departing from the scope of the present invention.

EXAMPLE 1

Preparation of Herbal Pharmaceutical Composition (SB221)

Herbal pharmaceutical composition 1 of the present invention was prepared as follows:

1. About 20 grams of each of the root of scutellaria, the rhizome of coptis, and ginseng, and about 40 grams of the root/rhizome of rhubarb, in the form of "Yin Pian" (meaning "drinking pieces"), which contained small thin slices of the herb that were ready for decoction use, were individually measured.

2. The herbs of (1) were individually ground in a grinder into individual powder forms.

3. The individually measured herbs of the root of scutellaria and the rhizome of coptis were separately simmered and/or boiled in about 20 volumes of water for about 60 minutes to produce the herbal extracts of the root of scutellaria and the rhizome of coptis separately.

4. The individually measured herbs of the root/rhizome of rhubarb were extracted under refluxing in about 20 volumes of alcohol : water (95:5, v/v) for about 60 minutes to produce the rhubarb extract.

5. The individually measured herbs of the root of were extracted under refluxing in about 20 volumes of alcohol: water (50:50, v/v) for about 60 minutes to produce the extract.

6. The individually filtered herbal extract of (6) were separately condensed under condensed pressure in a 50° C. water bath until an herbal paste was formed.

7. An adequate amount of corn starch (excipient) was added to and thoroughly mixed with each of the herbal pastes of the root of scutellaria, the rhizome of coptis, the root/rhizome of rhubarb, and the root of ginseng, and each of the corn-starch added herbal pastes is subject to drying treatment, until each of the herbal pastes becomes concentrated powders.

8. The concentrated powders from all of the four herbal pastes (i.e., the root of scutellaria, the rhizome of coptis, the root/rhizome of rhubarb, and the root of ginseng) were thoroughly mixed, and sieved through a 100-mesh sieve to form mixed powders.

9. Optionally, additional corn starch was added to the mixed powders and then subject to granulation in a Flow bed to form granules.

10. The granules are sieved again to form the SB221 granules, which were considered to be the semi-finished product of the present pharmaceutical composition.

11. The SB221 granules are filled into size 0 hard gel capsules, which were considered to be the finish drug product of the present pharmaceutical composition.

Pharmacological Studies

Study 1

Effects of SB221 on Vasodilation in WKY and SHR Rats

I. Study Design:
Instrument and Equipment:
Blood tension measurement equipment (Biopac System MP150); biosafe sterile operating station; Dynex MRX Revelation microplate reader; Nikon TRADE SECRET-100 inverted microscope; Galaxy R $CO_2$ incubator.

Reagents:
CD31 (PECAM-1) (Santa Cruz Cat. SC-1506); Collagenase (Sigma Cat. C-5138); Endothelial cell growth supplements, ECGs (Sigma Cat. E-9640); Acetylcholine, ACh (Sigma Cat. A6625); $N^W$-nitro-L-Arginine (L-NNA) (Sigma Cat. N-5501); Tetraethylammonium Chloride (Sigma Cat.T-2265); Phenylephrine (L-form)(Sigma Cat. P-6125); N-2-hydroxyethylpiperazine-N'-2-ethane sulfonic acid, HEPES (Sigma Cat. H-3375); Albumin bovine, BSA (Sigma Cat. A-4503); Ethylenediaminetetraccetic acid, EDTA (Sigma Cat.EDS); Glucose (Sigma Cat.G-8270); Magnesium sulfate, $MgSO_4$ (Sigma Cat.M-7506); 3-(4,5-dimethylthiazol-2-yl)-2,5-diphenyltetrazolium bromide, MTT (Sigma Cat. M-5655); Collagen (Vitrogen 100); Fetal Bovine Serum, FBS (Gibco Cat. 10270-106); Glutamine (Gibco Cat. 25030-081); M199 (Gibco Cat.31100-35); Penicillin/streptomycin (P/S) (Gibco Cat.15140-122); Pyruvate (Gibco Cat.11360-070); Trypsin-EDTA (Gibco Cat. 15400-054); Lactate dehydrogenase, LDH (Promega Cat. G1780); Potassium dihydrogen phosphate, $KH_2PO_4$ (Merck Cat.1.04873.0250); Sodium chloride, NaCl (Merck Cat.1.06404.1000); Sodium hydrogen carbonate, $NaHCO_3$ (Merck Cat.1.06329.0500); Dimethylsulfoxide (DMSO) (Cat. 1.09678.0100); Potassium chloride, KCl (Showa Cat.SE-3439K); Calcium chloride anhydrous, $CaCl_2$ (Junsei Cat.4-22).

Study Animal:
Eight-week-old male WKY rats and spontaneous hypertensive rats (SHR) from Charles River Laboratories were used in this study. The animals were kept at 22±2° C. in an air-conditioned animal room under 12-hour dark/light cycle (lights on during 7:00-19:00). The animals were given unrestricted water and food.

Test Solutions:
a. Krebs-Henseleit (KH) buffer pH 7.4, containing 118 mM NaCl; 24 mM $NaHCO_3$; 4.7 mM KCl; 1.2 mM $KH_2PO_4$; 1.2 mM $MgSO_4$; 1.7 mM $CaCl_2$; 30 μM EDTA; 10 mM glucose in double-distilled water.

b. M199 pH7.4 solution, prepared by dissolving 2.2 g $NaHCO_3$; 4.8 g HEPES; 1 package of M199; 10 mL P/S; 15-17 mg heparin, 10 mL pyruvate and 10 mL glutamine in 1 L of double-distilled water.

II. Method:
Treatment:
WKY and SHR rats were separated into 4 groups in accordance with their respective ages: (a) 12 weeks; (b) 15 weeks, (c) 18 weeks and (d) 25 weeks. Each age group was further subdivided into Control and SB221 subgroups. The SB221 treatment groups were treated with 180 mg/kg of SB221 via gavage (dosing with a 18 mg/mL SB221 solution at 10 mL/kg). The control groups were given equal volume of water. The animals were treated daily consecutively for 4 weeks. The animals were sacrificed and sampled for the blood vessel tests and immunohistological stain assays within a preset time limit during the day after completion of treatment.

Preparation of Blood Vessel Sections:

a. Before initiation of the experiment, a circulated water bath was turned on with temperature set at 37° C.

b. About 10~20 mL of KH buffer were placed in each of three (3) Petri dishes. The buffer was aerated with 95% $O_2$/5% $CO_2$.

c. After the animal was anesthetized, the thoracic cavity of the animal was opened to expose the heart. Blood was drawn from the heart. The section from the arch of the aorta to the thoracic aorta above the diaphragm was dissected out and immediately placed in the oxygenated Petri dish.

d. The connective tissues and branch vessels of the thoracic aorta were cut away using a pair of ophthalmologic scissors. After carefully cleaning away blood clot in the aorta, the aorta was cut into 2-4 sections (each about 2-3 mm long) using surgical blade. Each of the aortic sections was hooked up by a blood vessel hook and carefully placed in a chamber. According to the numbers of animals, the aortic sections could be separated into 4-8 chambers.

e. The baseline tension of the aortic section was adjusted to 2 g and maintained for 30 minutes, then the tension measurement was conducted.

Vasodilation Test:

The aortic sections were first allowed to be contracted with $10^{-6}$ M phenylephrine. After the contraction was stabilized, $10^{-9}$~$10^{-6}$ M acetylcholine (ACh) were added to the aortic sections. The rate of vasodilation of the aortic section was observed to determine whether the function of the endothelial cells was normal.

Statistical Analysis

The changes in tension were expressed as relaxation %. The maximum contraction was expressed by the contracting tension at the highest concentration of the inducer. Not only each animal can show different response to the test chemicals, different aortic sections in one animal can also show different response to the test chemicals. Therefore, the results from each aortic section were treated as independent data during data analysis and the results were expressed as mean ± standard deviation (SD). Comparisons between groups were carried out using two-factor ANOVA. Further Post Hoc analysis using Student-Newman-Keuls' test was carried out on those data showed significant difference in the ANOVA. The significance level was preset at p<0.05.

Results

Figure 2:
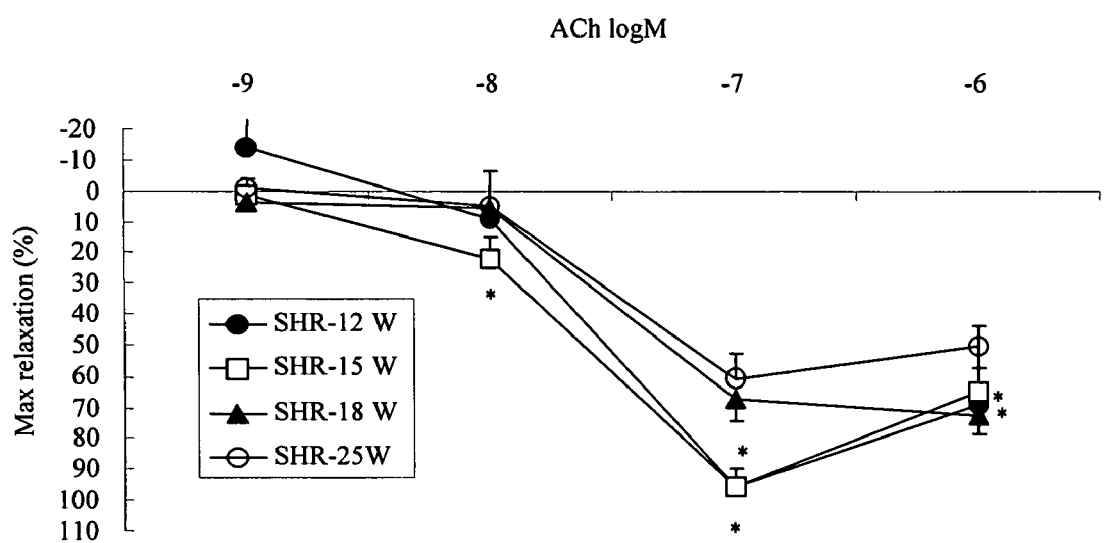
FIG. 2 compares the vasodilation in response to acetylcholine in various ages of SHR rats: SHR-12W control (●); SHR-15W control (□) SHR-18W control (▲) and SHR-25W control (○). * indicates that the vasodilation of the specified group was statistically different (p<0.05, two-factor ANOVA) from that of the SHR-25W control group.

As shown in FIG. 2, Ach induced vasodilation in the aortas of the SHR control rats. The % relaxation (i.e., vasodilation) increased as the Ach concentration increased from $10^{-9}$ M to $10^{-7}$ M, showing maximal rate of vasodilation at $10^{-7}$ M. At $10^{-8}$ M of Ach, the mean rate of vasodilation of the SHR-25W control rats was about 14% different (which was statistically significant [p<0.05]) from that of the SHR-15W control rats. At $10^{-7}$ M of Ach, the mean rate of vasodilation of the 25-week-old SHR control rats was about 29% different (which was statistically significant [p<0.05]) from that of the SHR-12W and SHR-15W control rats. At $10^{-6}$ M Ach, the mean rate of vasodilation of the 25-week-old SHR control rats showed significant 13% and 16% differences from those of the SHR-12W and SHR-15W control rats, respectively. These results showed that the vasodilation function of the SHR control rats deteriorated as rats aged, suggesting that the function of the endothelial cells in the blood vessels deteriorated over time.

Figure 3:
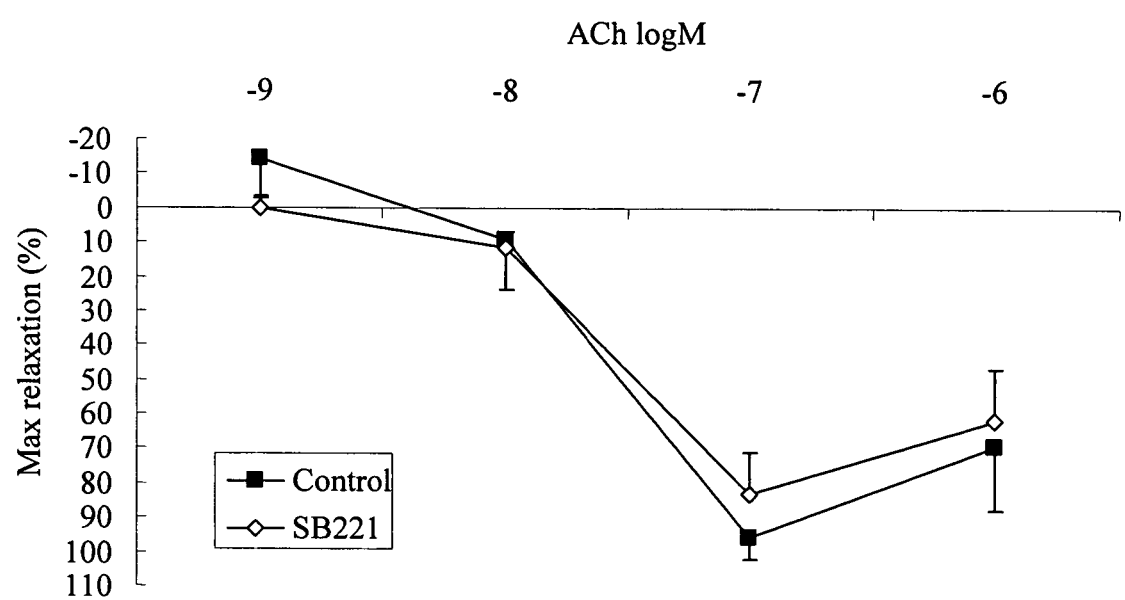
FIG. 3 compares the vasodilation in response to acetylcholine of 12-week-old SHR rats: control (■) and SB221 (◇) groups. The SB211 group was provided with the pharmaceutical composition of the present invention.
Figure 4:
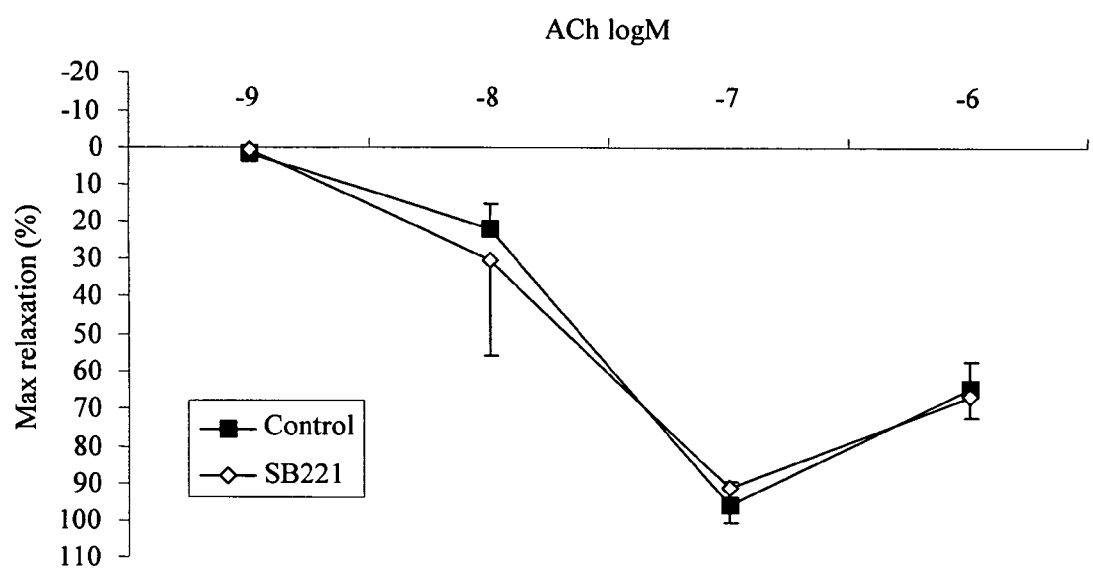
FIG. 4 compares the vasodilation in response to acetylcholine of 15-week-old SHR rats: control (■) and SB221 (◇) groups. The SB211 group was provided with the pharmaceutical composition of the present invention.

As shown in FIGS. 3 and 4, the mean max. relaxation % (i.e., vasodilation) of the SHR-12W SB221, SHR-12W control, SHR-15W SB221, and SHR-15W control rats were 83%, 95%, 91% and 96%, respectively. There was no significant difference in vasodilation between the control and SB221 groups, indicating that the SB221 treatment had no significant effects on the 12 and 15-week-old SHR rats.

Figure 5:
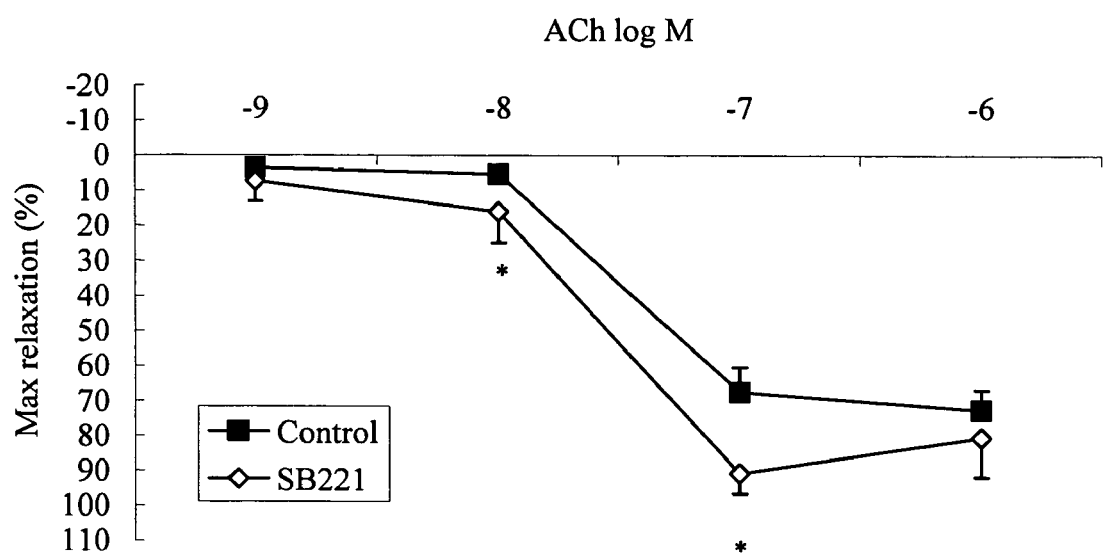
FIG. 5 compares the vasodilation in response to acetylcholine of 18-week-old SHR rats: control (■) and SB221 (◇) groups. The SB211 group was provided with the pharmaceutical composition of the present invention. * indicates that there was a statistically significant difference in vasodilation between the SB221 group and the control group (p<0.05, two-factor ANOVA).

As shown in FIG. 5, the maximal % relaxation (i.e., vasodilation) of the SHR-18W SB221 and SHR-18W control rats occurred at $10^{-7}$ M of Ach, which gave a max. relaxation % of about 90.7% for the SHR-18W SB221 rats and about 68% for the SHR-18W control rats. This gave a statistically significant difference of about 23%. At $10^{-8}$ M of Ach, the SHR-18W SB221 rats showed a statistically significant difference (P<0.05) of about 37% between the SHR-18W SB221 and the SHR-18W control rats. The results indicate that the SB221 treatment improved the function of the endothelial cells by increasing the max. % of relaxation in the 18-week-old SHR rats.

Figure 6:
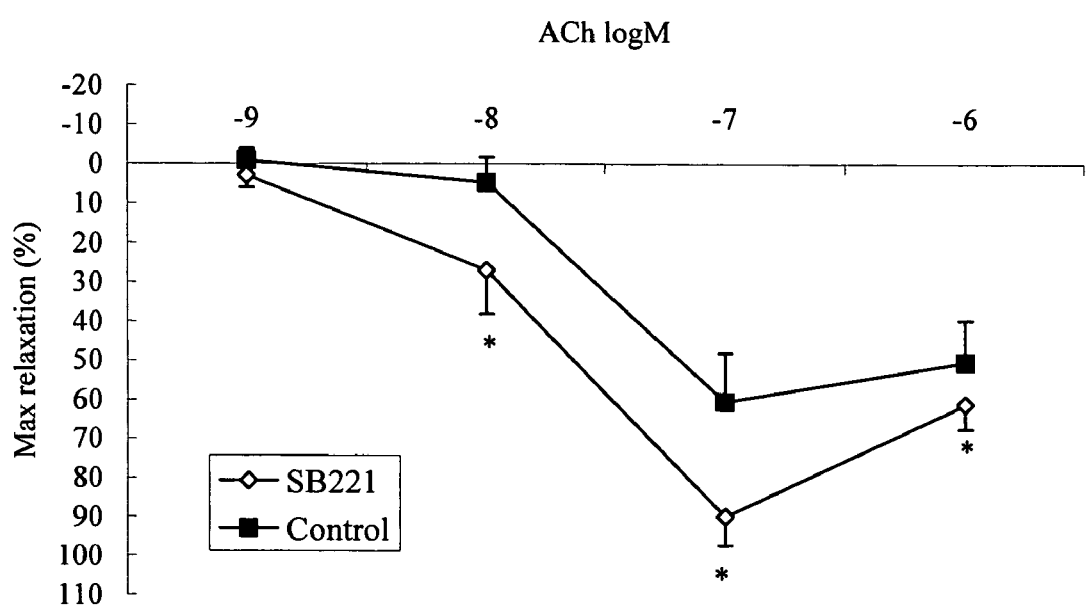
FIG. 6 compares the vasodilation in response to acetylcholine of 25-week-old SHR rats: control (■) and SB221 (◇) groups. The SB211 group was provided with the pharmaceutical composition of the present invention. * indicates that there was a statistically significant difference in vasodilation between the SB221 group and the control group (p<0.05, two-factor ANOVA).

As shown in FIG. 6, the SHR-25W SB221 and control groups showed max. relaxation % (i.e., vasodilation) at $10^{-7}$ M of Ach, where the max. relaxation % of the SHR-25W SB221 and control rats were about 90% and about 67%, respectively. This showed a statistically significant difference of about 23.2%. At $10^{-8}$ and $10^{-6}$ M of Ach, the SHR-25W SB221 rats showed a significant difference of about 19% and about 12% in the maximal relaxation % from the SHR-25W control rats. The results indicate that the SB221 treatment improved the function of the endothelial cells in the blood vessels of the 25-week-old SHR rats.

Figure 7:
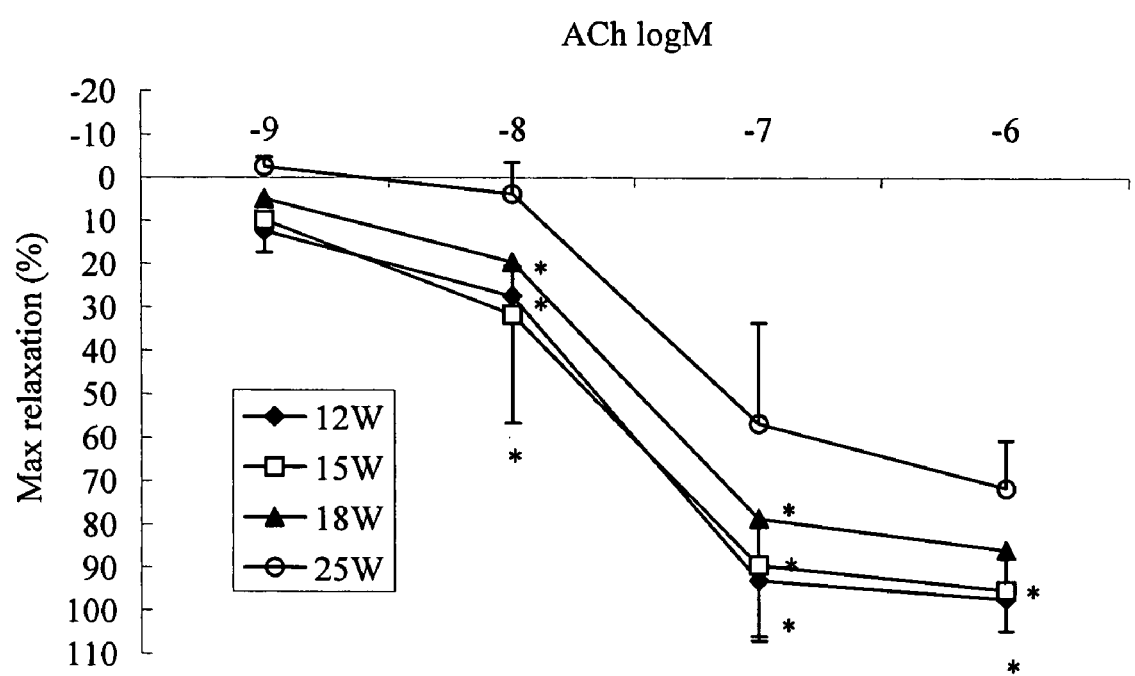
FIG. 7 compares the vasodilation in response to acetylcholine in various ages of WKY rats: WKY-12W control (♦); WKY-15W control (□); WKY-18W control (▲) and WKY-25W control (○). * indicates that the vasodilation of the specified group was statistically different (p<0.05, two-factor ANOVA) from that of the WKY-25W control group.

As shown in FIG. 7, at $10^{-8}$ M of Ach, the WKY-25W control rats showed significant differences of about 21%, about 25% and about 13% in max. relaxation % (i.e., vasodilation) from the WKY-12W control, WKY-15W control and WKY-18W control rats, respectively. At $10^{-7}$ M of Ach, the WKY-25W control rats showed significant differences of about 35%, about 31% and about 21% in max. relaxation % from the WKY-12W control, WKY-15W control and WKY-18W control rats, respectively. At $10^{-6}$ M of Ach, the WKY-25W control rats showed significant differences of 25% and 23% in vasodilation from the WKY-12W control and WKY-15W control rats, respectively. These results show that the vasodilation function of the WKY control rats deteriorated as rats aged, indicating deterioration of the function of the endothelial cells.

Figure 8:
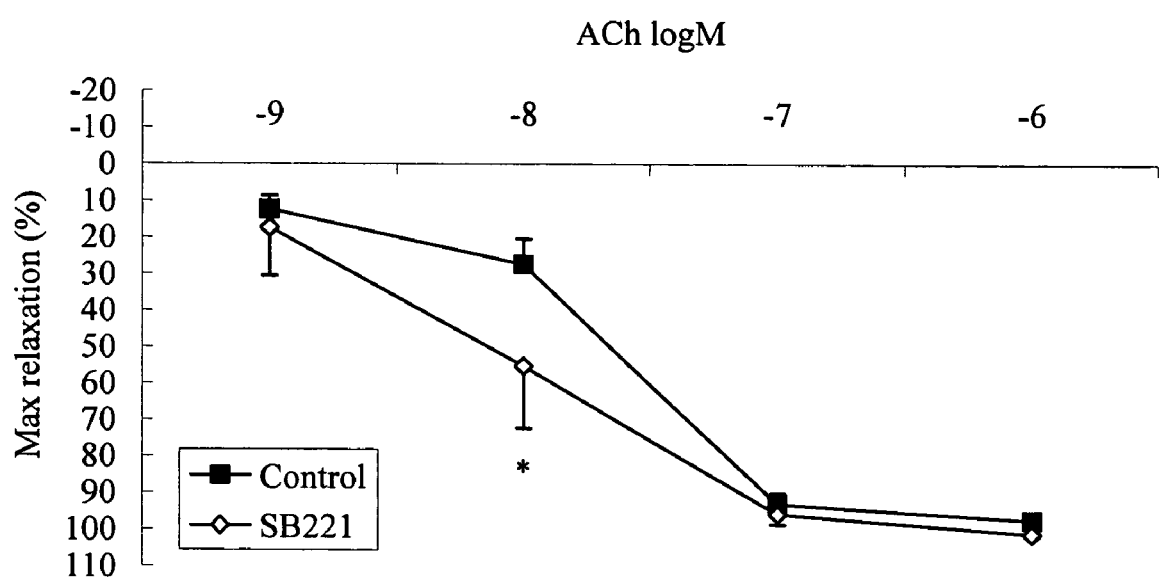
FIG. 8 compares the vasodilation in response to acetylcholine of 12-week-old WKY rats: control (■) and SB221 (◇) groups. The SB211 group was provided with the pharmaceutical composition of the present invention. * indicates that there was a statistically significant difference in vasodilation between the SB221 group and the control group (p<0.05, two-factor ANOVA).
Figure 9:
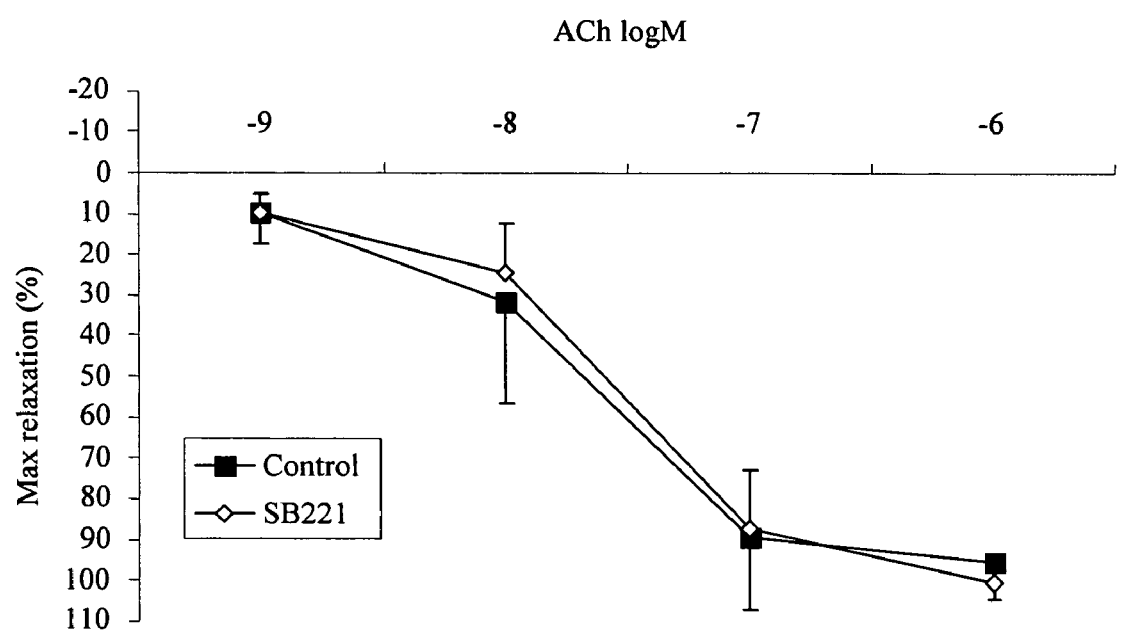
FIG. 9 compares the vasodilation in response to acetylcholine of 15-week-old WKY rats: control (■) and SB221 (◇) groups. The SB211 group was provided with the pharmaceutical composition of the present invention.

As shown in FIGS. 8 and 9, the max. relaxation % (i.e., vasodilation) of the WKY-12W and WKY-15W rats increased as the Ach concentration increased from $10^{-9}$ M to $10^{-6}$ M, showing maximal vasodilation at $10^{-6}$ M. At $10^{-9}$, $10^{-7}$ and $10^{-6}$ M, there were less than about 5% differences between the % relaxation of the WKY-12W SB221 and control rats. At $10^{-8}$ M, there was a significant difference of about 28% between the max. relaxation % of the WKY-12W SB221 and the control rats. The max. relaxation % in the WKY-15W SB221 rats and the control rats were about 100% and about 95%, respectively. The results show insignificant difference in the function of the endothelial cell of the WKY-15W rats, regardless of the SB221 treatment.

Figure 10:
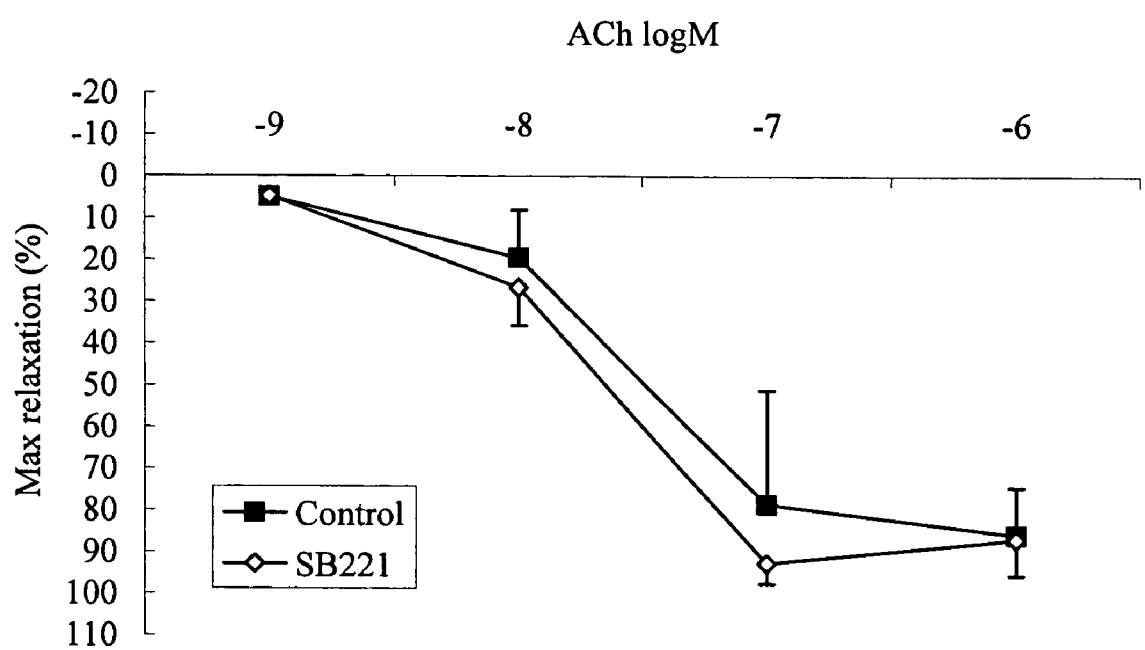
FIG. 10 compares the vasodilation in response to acetylcholine of 18-week-old WKY rats: control (■) and SB221 (◇) groups. The SB211 group was provided with the pharmaceutical composition of the present invention.

As shown in FIG. 10, the WKY-18W SB221 and control rats showed max. relaxation % (i.e., vasodilation) at $10^{-7}$ and $10^{-6}$ M of Ach. The max. relaxation % of the WKY-18W SB221 rats and the control rats were about 94% and about 86%, respectively. There was no significant difference in vasodilation between the SB221 group and the control group, indicating that the SB221 treatment had no significant effects on the futnction of the endothelial cells among the WKY-18W rats.

Figure 11:
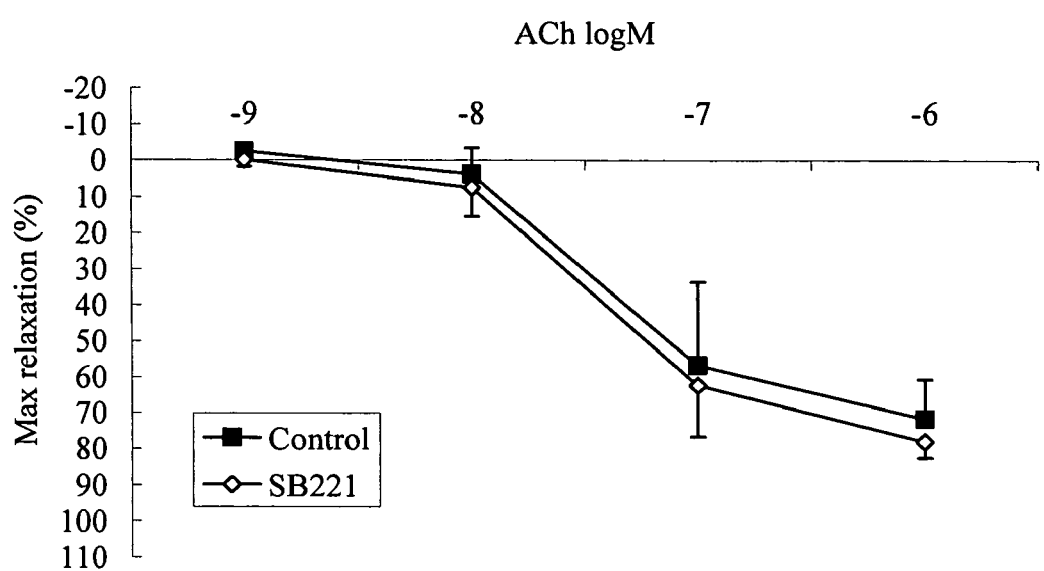
FIG. 11 compares the vasodilation in response to acetylcholine of 25-week-old WKY rats: control (■) and SB221 (◇) groups. The SB21 1 group was provided with the pharmaceutical composition of the present invention.

As shown in FIG. 11, the max. relaxation % (i.e., vasodilation) of the WKY-25W rats increased as the Ach concentration increased from $10^{-9}$ M to $10^{-6}$ M. The max. relaxation % of the WKY-25W SB221 rats and the control rats were about 78% and about 73%, respectively. There was no significant difference in vasodilation between the SB221 and control groups, indicating that the SB221 treatment had no significant effects on the function of the endothelial cells in the blood vessels of the WKY-25W rats.

In sum, the results of the vasodilation studies in the normal blood pressure (WKY) rats demonstrate that the max. relaxation % of normal rats decreased generally and significantly over age (FIG. 7), showing deterioration of the function of endothelial cells in the blood vessels due to aging. However, the treatment of SB221 to the WKY rats did not show significant difference in the vasodilation, suggesting that the effects of SB221 in normal blood pressure rats were not significant (FIGS. 8-11).

Contrary to the findings in WKY rats, however, when the SHR rats were used to study the vasodilation effects on various ages of the animals, as shown in FIG. 2, the max. relaxation % decreased significantly over age ($p<0.05$) between the 12 W group and the 25 W group, demonstrating that similar to those occurred in the WKY rats, aging contributed to the change in vasodilation. However, unlike what was shown in the WKY rats (FIG. 7), when maximal Ach ($10^{-6}$ M) was given, the max. relaxation % in the SHR-25W group was about 50% (FIG. 2), as opposed to that of the 25 W WKY rats which was about 70% (FIG. 7), which served as an indication that the SHR rats developed potential hypertension when they aged. Also, as shown in FIGS. 8-11, there was a significant difference ($p<0.05$) in max. relaxation % between the Control and the SB221 Groups in the SHR rats, indicating that SB221 demonstrated effect on inhibiting the development of hypertention and the reduction of vasodilation.

The results of this study showed that the effects of SB221 in normal blood pressure rats were not significant. However, SB221 demonstrated significant blood pressure lowering effect in hypertension animals by significantly increasing the dilation the vessel, probably through protective effects on the vascular endothelium in preventing the degeneration of endothelial cells.

Discussion

Through the functional test using endothelium-dependent vasodilator (i.e., ACh), it was shown that SB221 demonstrated preventive effect on the degeneration of the endothelial cells.

The degeneration of the endothelial cells in both the WKY and SHR rats due to aging was probably due to the following reasons: (1) damages of Gαi proteins; (2) reduction in the secretions of NO, prostacyclin and endothelium-derived hyperpolarizing factor (EDHF); (3) increase in the secretion of endoperoxides; (4) increase in the production of reactive oxygen species; (5) increase in the production of endothelin-1; and (6) reduction in the sensitivity of vascular smooth muscle cells toward NO, prostacyclin and EDHF. The same phenomenon also was found in the elders and hypertensive human patients. Through measuring the arterial blood flow at the upper arm, it was found that these two human populations tend to lose the functions in the NO pathway and increase in the production of cyclooxygenase-dependent vasoconstrictor.

Conclusion

This study showed that SB221 not only have the effects in lowing blood pressure, but also have endothelial protective activity in SHR rats of 18 weeks of age or above.

Study 2

Protective Effects of SB221 on Endothelial Cells: Morphologic Study Using CD31 Immunohistochemistry Method Platelet/endothelial cell adhesion molecule-1 (PECAM-1), also referred to as CD31, is a glycoprotein expressed on the cell surfaces of monocytes, neutrophils, platelets and certain T cells, endothelial cells (See Simmons et al. *J. Exp. Med.* 1990; 171:2147-2152; Berman et al. *J. Immunol.* 1996; 156:1515-1524, which are herein incorporated by reference). CD31 is a single-chain glycoprotein of 130-140 kD. Detection of CD31 using PECAM-1 antidoby by Western blotting, immunoprecipitation and immunohistochemistry (with paraffin-embedded sections) has been employed in the morphology study of the endothelial cells.

In the following paragraphs, morphological study of the aortic sections prepared according to Study 1, supra, was carried out using an affinity purified goat polyclonal antibody raised against a peptide mapping at the carboxy terminus of the PECAM-1 of mouse origin to detect the CD31 via the immunohistochemistry method.

Method:

The instrument/equipment, reagents, test solutions, animals, animal treatments, and blood vessel sectioning were the same as those described in Study 1, supra.

CD31 immunohistochemistry staining

The aortic sections were soaked in 10% formalin and later embedded in paraffin and sectioned. CD31 immunohistochemistry staining were performed on the paraffin sections. Several stain chambers were prepared as xylene 1 (containing 100% xylene), xylene 2 (100% xylene), xylene 3 (100% xylene), 100% ethanol, 95% ethanol, 75% ethanol, 50% ethanol and 100% water. The paraffin sections were first sequentially placed in xylene 1, xylene 2, and xylene 3 for 10 minutes each, then sequentially placed in the 100%, 95%, 75%, 50% ethanol and then water for 5 minutes each. The paraffin sections were then placed in a box containing a solution of 3% $H_2O_2$/methanol (¼) for 10 minutes; rinsed off excessive solution; and sequentially placed in 0.1% trypsin at 37° C. for 30 minutes and 3% BSA blotting for 70 minutes. After pouring off the solution and adding the primary antibody for CD31 at 1:300, the paraffin sections were stored at 4° C. overnight. Then the paraffin sections were removed from the solution and sequentially placed in the link antibody solution, streptavidin peroxidase solution for 15 minutes each. The paraffin sections were stained with DAB. Between the change of solutions, the sections were washed 5 times with PBS, each time lasted for 5 minutes. After staining, the paraffin sections were observed under microscope.

Statistical Analysis

The results of CD31 immunohistochemistry staining were visually evaluated.

Figure 14:
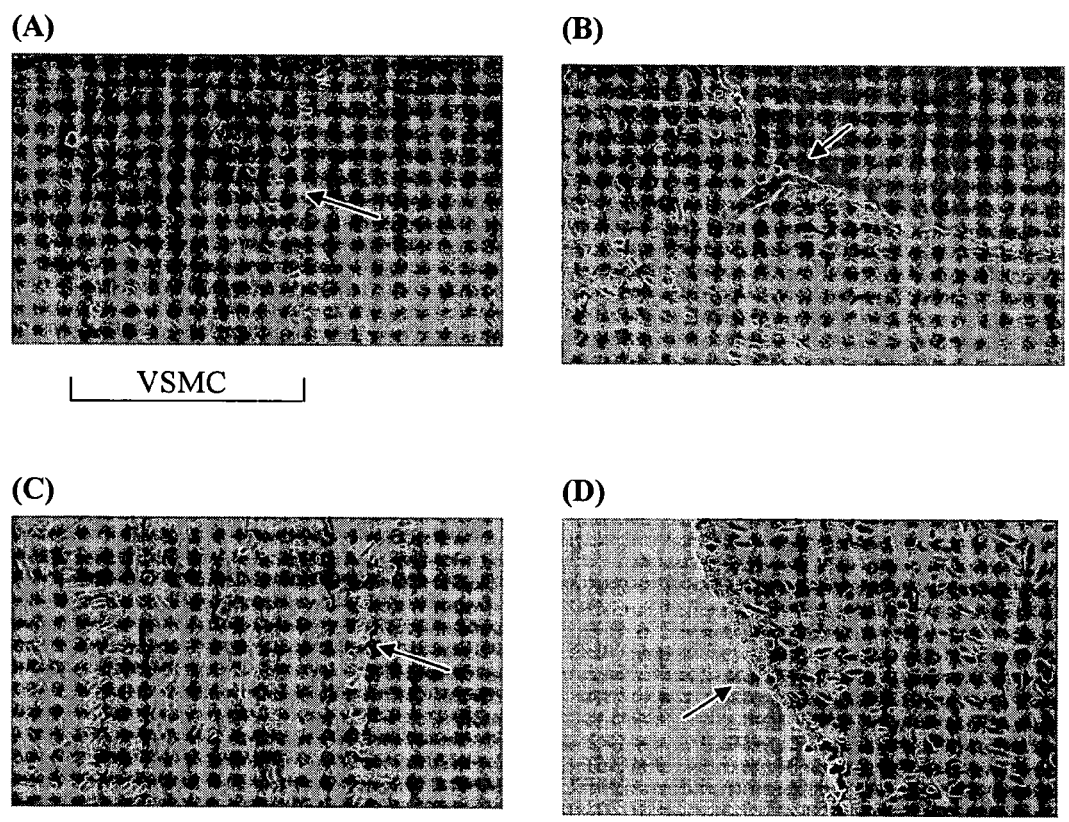
FIG. 14 shows the CD31 immunohistochemical staining of the cross section of the thoracic aortic tissue in the SHR control rats: (A) SHR-12W control, (B) SHR-15W control, (C) SHR-18W control, and (D) SHR-25W control. CD31 is a widely distributed, single-chain glycoprotein of mass 130-140 kD found on leukocytes (T and B cells, monocytes, granulocytes, platelets, 40% of bone marrow cells), endothelial, and smooth muscle cells. Figures were taken at 400× under optical microscope using CD31 antibody at 1:300 concentration. Arrows depict the endothelial cells, which compose of a layer of cells that lines the cavities of the blood vessels. The endothelium (the layer of the endothelial cells) shown in (C) and (D) contains uneven and partially peeled off surfaces, exposing some of the mesothelial layer.

Results:

As shown in FIG. 14, the endothelium of the SHR-12W control rats (A) and the SHR-15W control rats (B), respectively, was intact and had smooth surfaces. However, the endothelium of the SHR-18W control rats (C) and the SHR-25W control rats (D), respectively, had uneven and partially peeled off surfaces. The results indicated that the SHR rats with ages on or above 18 weeks had damaged endothelium.

Figure 15:
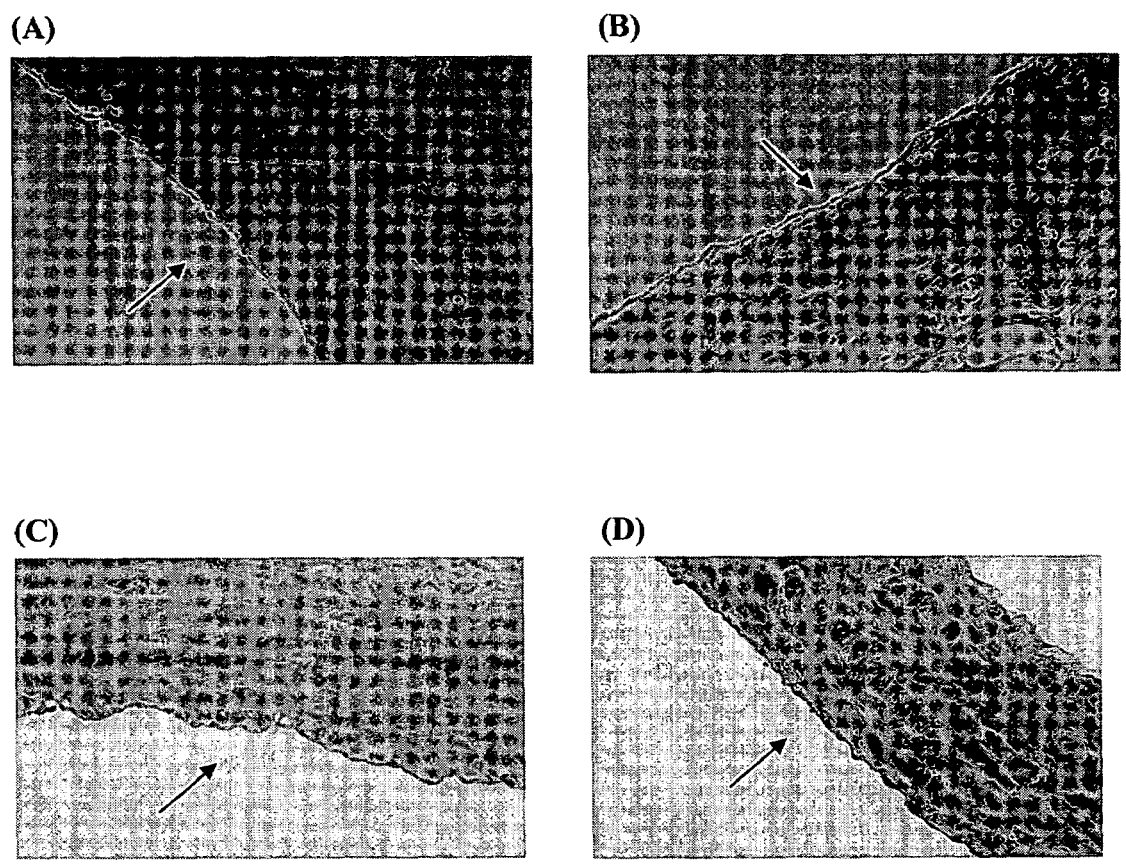
FIG. 15 shows the CD31 immunohistochemical staining of the cross section of the thoracic aortic tissue in the SHR rats treated with SB221: (A) SHR-12W SB221, (B) SHR-15W SB221, (C) SHR-18W SB221, and (D) SHR-25W SB221. Figures were taken at 400× under optical microscope using CD31 antibody at 1:300 concentration. Arrows depict the endothelial cells. The endothelial cells in all age groups, after the treatment of SB221, contain smooth and even surfaces, contrary to the endothelial cells of the 18 weeks and 25 weeks rats without SB221 treatment (see (C) and (D) of FIG. 14), which had uneven and partially peeled off surfaces.

As shown in FIG. 15 (A)-(D), the endothelium of the SHR-12W SB221, SHR-15W SB221, SHR-18W SB221, and SHR-25W SB221 rats, respectively, was intact and contained smooth surfaces. The results indicate that the SB221 had protective effect on endothelial cells of the SHR rats, which prevented the cells from being degenerated after 18 or more weeks of age.

Figure 16:
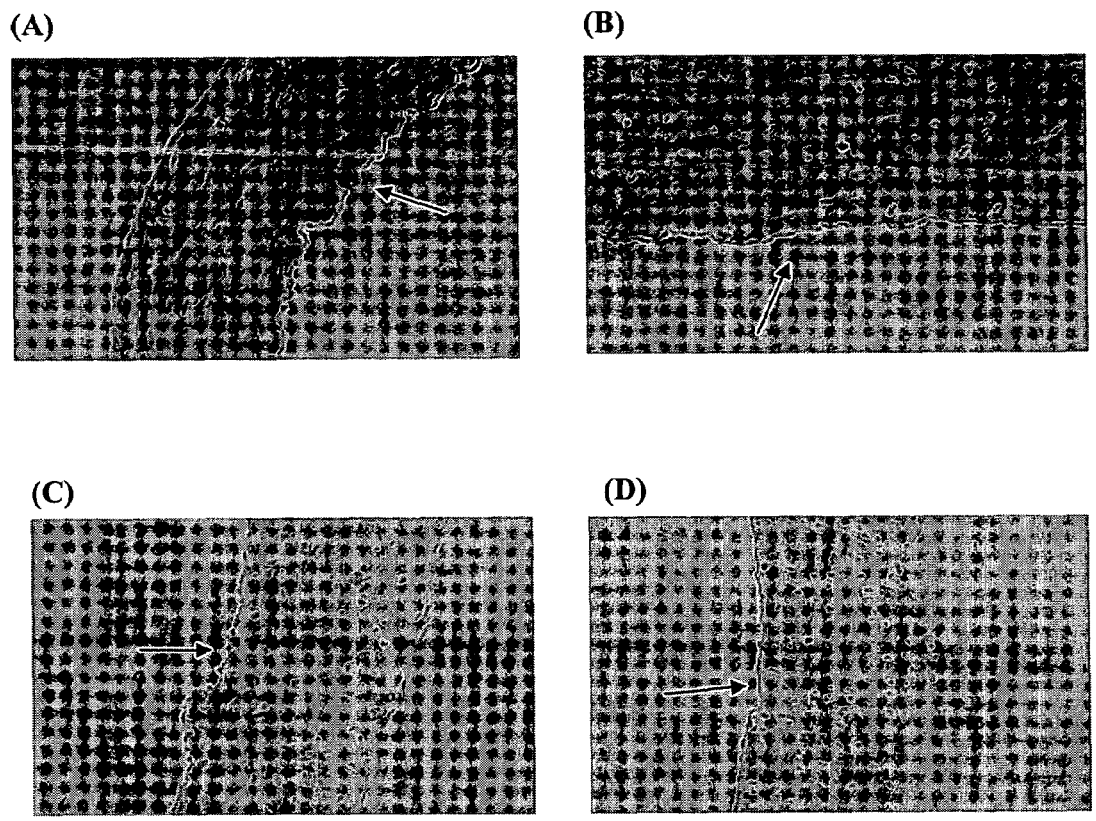
FIG. 16 shows the CD31 immunohistochemical staining of the cross section of the thoracic aortic tissue in the WKY control rats: (A) WKY-12W control, (B) WKY-15W control, (C) WKY-1 8W control, and (D) WKY-25W control. Figures were taken at 400× under optical microscope using CD31 antibody at 1:300 concentration. Arrows depict the endothelial cells. The endothelial cells of the WKY control rats demonstrate smooth and even surfaces.

As shown in FIG. 16, the endothelium of the WKY-12W control, WKY-15W control, WKY-18W control, and WKY-25W control rats, respectively, was intact with smooth surfaces. The results indicate that the endothelial cells of the WKY rats did not deteriorate upon age ranged between 12 weeks and 25 weeks.

Figure 17:
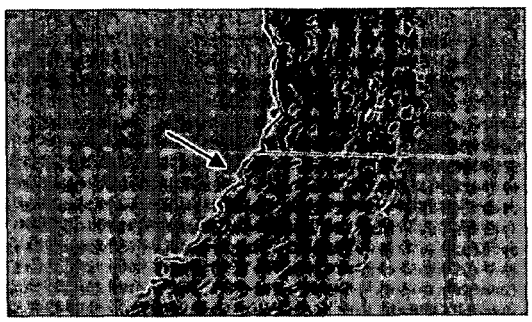
FIG. 17 shows the CD31 immunohistochemical staining of the cross section of the thoracic aortic tissue in the WKY rats treated with SB221: (A) WKY-12W SB221, (B) WKY-15W SB221, (C) WKY-18W SB221, and (D) WKY-25W SB221. Figures were taken at 400× under optical microscope using CD31 antibody at 1:300 concentration. Arrows depict the endothelial cells. After treatment with SB221 (the pharmaceutical composition of the present invention), the endothelial cells in the WKY rats demonstrate smooth and even surfaces.
Figure 17:
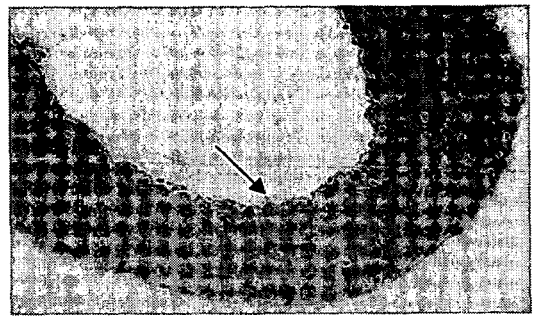
Figure 17:
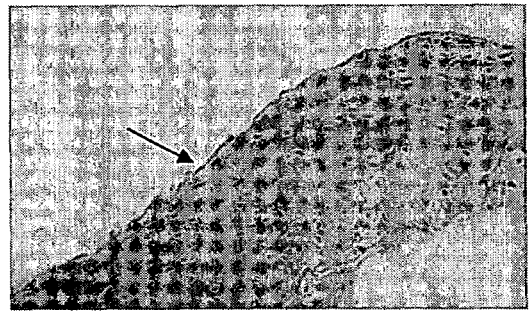
Figure 17:
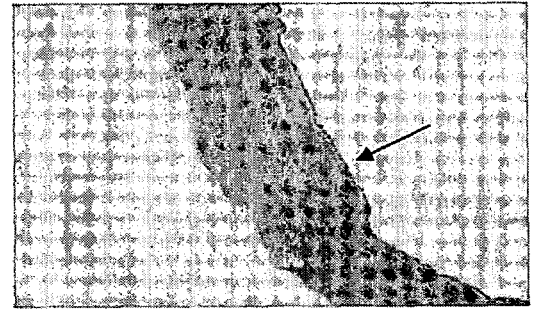

As shown in FIG. 17, the endothelium of the WKY-12W SB221, WKY-15W SB221, WKY-18W SB221, and WKY-25W SB221 rats, respectively, was intact with smooth surfaces. The results indicated treatment with SB221 did not affect the morphology of the endothelial cells of the WKY rats.

Study 3

Cytotoxicity Studies of SB221 in Human Umbilical Vein Endothelial Cells (HUVEC)

As an abundant and easily accessible endothelial cell type, HUVEC are often used as a tool in cardiovascular research to investigate angiogenesis and cardiac diseases.

The cytotoxicity effects of SB221 on HUVEC were studied using the lactate dehydrogenase (LDH) assay and the MTT assay. When plasma membranes of cells are disrupted by the test drug, the cytosolic LDH is released into the surrounding medium. Thus, lower measurement of the LDH activity indicates less cytotoxicity of the test drug. On the other hand, MTT (3-(4,5-dimethylthiazol-2-yl)-2,5-diphenyltetrazolium bromide) is a water-soluble tetrazolium dye. Active mitochondrial dehydorgenases of living cells convert the yellowish MTT to an insoluble dark purple formazan. This conversion does not take place in dead cells. The water-insoluble formazan can be isolated, dissolved in an organic solvent and quantified spectrophotometrically. Thus, higher measurement of the formazan indicates lower cytotoxicity of the test drug.

Materials:

The HUVEC were provided by Dr. K. C. Lin, President of LongShan Women's and Children's Hospital, ChungHo, Taipei Hsien, Taiwan. Samples of human umbilical cord was placed in sterile PBS buffer. Collagenase type I was placed into the solution. The endothelial cells were washed by repeated suction/release of the solution. The cells were cultivated in the M199 medium containing 20% serum, endothelium culture growth solution (ECGs) 15 mg/mL at 37° C. in a 5% $CO_2$/95% air incubator. The culture medium was changed next day and then every other days (Jaffe et al. *J. Clin. Invest*. 1973; 52:2745-2756).

Other reagents were the same as those described in Study 1, supra.

Method:

1. LDH Assay

After the HUVEC cells were confluent in the culture bottles, the cells were suspended by a trypsin-EDTA solution. The suspended cells were then placed in the 96-well culture plate at $5\times10^3$ cells/well. The control group was grown in the M199 medium containing no FBS to provide a basal reference value of no cytotoxicity. The experimental groups were grown in the M199 media containing various concentration of SB221. After 4 hours, the culture media were collected and uniformly mixed with equal volumes of LDH kit reagent. The mixtures were kept at room temperature for 30 minutes with protection from light exposure. Then the stop reagent at volumes equivalent to those of the culture media were added to the mixtures. The reaction results were then detected at 490 nm wavelength. A total lysate of the cells were also included in the experiment to provide a reference value for 100% cytotoxicity. The results of LDH activity were expressed as % cells lysate and calculated by setting the absorbance of the total lysate group to 100%.

2. MTT Assay

After the HUVEC cells were confluent in the culture bottles, the cells were suspended by adding a trypsin-EDTA solution to the culture medium. The cells were placed in the 96-well culture plate at $5\times10^3$ cells/well. The cells were then incubated in the M199 medium for 24 hours. The control group was then cultured in the M199 medium to provide the basal reference value. The experimental groups were cultured in the M 199 media containing various concentrations of SB221. After 24 hours, the culture media were replaced with fresh culture media containing 100 μL of 0.5 mg/mL MTT. The cells were cultivated in a 37° C. incubator for 2 hours. After the removal of MTT, DMSO was added to each wells to dissolve the cells. The absorbance of the solutions at 550 nm was measured using an ELISA reader. The difference in the absorbance was determined and the percentage was calculated by setting the absorbance difference of the basal control group to 100%.

Statistical Analysis

The results of the LDH and MTT assays were expressed as mean ± standard deviation (SD). The differences between groups were analyzed using one-factor ANOVA. Further Post Hoc Tukey test was carried out on the data showing significant differences in the ANOVA analysis. The significance level was preset at $p<0.05$.

Figure 12:
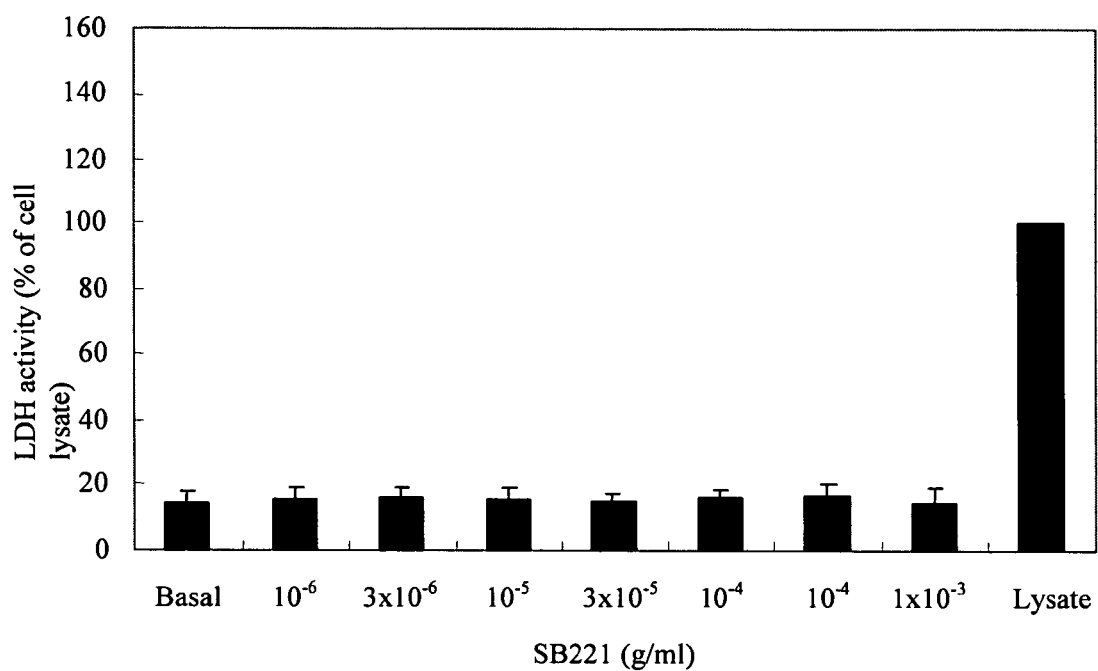
FIG. 12 shows the results of the cytotoxicity study of SB221 in the human umbilical vein endothelial cells (HUVEC) based on the lactate dehydrogenase (LDH) activity (expressed as % of cell lysate) (n=3) found in the cell medium. The results of LDH activity were compared to the basal LDH value (where the cells were grown without SB221) and whole cell lysate (where the cells were collected and homogenized). The whole cell lysate was represented as 100% LDH value. The results of this study show that there was no statistical difference in LDH activity between the basal group and the SB221 group (between $10^{-6}$ to $10^{-3}$ g/ml). The basal LDH activity of HUVEC was about 14% of the total lysate and the LDH activity of the SB221 group was within 3% difference from that of the basal group. The LDH activity in both the basal group and the SB221 group was significantly different that of the whole cell lysate.

Results:

As shown in FIG. 12, the LDH activity of the control group (basal value, representing no cytotoxicity) was about 14.0%, as compared to the total lysate group (representing 100% cytotoxicity). The LDH activities of the HUVEC cells treated with $1\times10^{-6}$ to $1\times10^{-3}$ mg/mL SB221 were within 3% differences from that ofthe basal value and were not significantly different from that of the basal value. The results of the LDH assay indicate that SB221 was not toxic to the endothelial cells.

Figure 13:
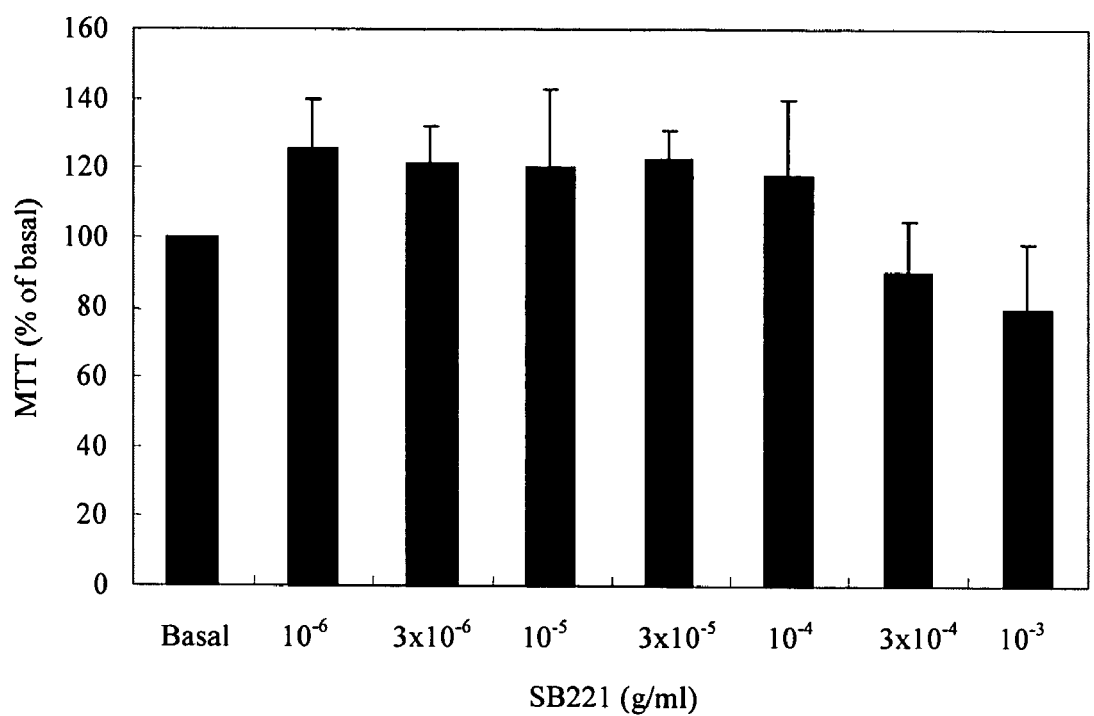
FIG. 13 shows the results of the cytotoxicity study of SB221 in human umbilical vein endothelial cells (HUVEC) based on MTT tetrazolium salt colorimetric assay (n=7) of the cell medium collected from the SB221 treated cells and the control cells (i.e., cells without SB221 treatment) which gave the basal value. Data analysis was carried out using one-factor ANOVA). The results show that there was no statistically significant difference between the control and the SB221 groups.

As shown in FIG. 13, SB221 has no cytotoxic effect on HUVEC. The MTT conversion by HUVEC cells treated with $1\times10^{-6}$ to $1\times10^{-3}$ mg/mL of SB221 ranged from 125.4% to 80.0% in comparison to that of the control group (basal value, no toxicity). There was no significant difference between the basal value and those of the SB221 groups. The results of the MTT assay indicate that SB221 was not toxic to the endothelial cells.

Conclusion:

SB221 was not cyctotoxic to the HUVEC.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A composition comprising:
   an extract of Radix Scutellariae (root of scutellaria);
   an extract of Rhizoma Coptidis (rhizome of coptis);
   an extract of Radix et Rhizoma Rhei (root and rhizome of rhubarb); and
   an extract of Radix Ginseng (root of ginseng);
   wherein said extract of said root of scutellaria, said extract of said rhizome of coptis, said extract of said root and rhizome of rhubarb, and said extract of root of ginseng are in dried form and are produced by extracting said root of scutellaria, said rhizome of coptis, said root and rhizome of rhubarb, and said root of ginseng with a solvent which is at least one selected from the group consisting of water and ethyl alcohol, and said root and rhizome of rhubarb are root and rhizome of *Rheum palmatum L*.

2. The composition according to claim 1, wherein said root of scutellaria, said rhizome of coptis, said root and rhizome of rhubarb, and said root of ginseng are at a weight ratio of about 1-2 :1-2 :1-2 :1-2.

3. The composition according to claim 2, wherein said root of scutellaria, said rhizome of coptis, said root and rhizome of rhubarb, and said root of ginseng are at a weight ratio of about 1 : 1 : 2 : 1.

4. The composition according to claim 1, wherein said root of scutellaria is extracted by water.

5. The composition according to claim 4, wherein said root of scutellaria extracted at about 98±5° C.

6. The composition according to claim 1, wherein said rhizome of coptis is extracted by water.

7. The composition according to claim 6, wherein said rhizome of coptis is extracted at about 98±5° C.

8. The composition according to claim 1, wherein said root and rhizome of rhubarb are extracted by about 95%ethyl alcohol at about 70±5° C.

9. The composition according to claim 1, wherein said root of ginseng are extracted by about 50% ethyl alcohol at about 70±5° C.

10. The composition according to claim 1, wherein said extract of root of scutellaria, said extract of rhizome of coptis, said extract of root and rhizome of rhubarb, and said extract of root of ginseng are individually filtered and condensed to form concentrated powders of said root of scutellaria, said rhizome of coptis, said root and rhizome of rhubarb, and root of ginseng individually, and wherein said individually concentrated powders of said root of scutellaria, said rhizome of coptis, said root and rhizome of rhubarb, and root of ginseng are mixed and granulated to produce granules of said composition.

11. The composition according to claim 10, wherein a pharmaceutically acceptable excipient or carrier is added before said condensing.

* * * * *